(12) United States Patent
Sigmon, Jr. et al.

(10) Patent No.: US 11,660,432 B2
(45) Date of Patent: May 30, 2023

(54) DILATION PROCEDURES WITH EXPANDABLE DILATION DEVICES

(71) Applicant: Cook Medical Technologies LLC, Bloomington, IN (US)

(72) Inventors: John Crowder Sigmon, Jr., Winston-Salem, NC (US); Shaun D. Gittard, Winston-Salem, NC (US); Gregory J. Hardy, Colonie, NY (US); Vihar Surti, Winston-Salem, NC (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 683 days.

(21) Appl. No.: 16/587,650

(22) Filed: Sep. 30, 2019

(65) Prior Publication Data
US 2020/0101271 A1    Apr. 2, 2020

Related U.S. Application Data

(60) Provisional application No. 62/739,521, filed on Oct. 1, 2018.

(51) Int. Cl.
*A61M 29/02* (2006.01)

(52) U.S. Cl.
CPC ....... *A61M 29/02* (2013.01); *A61M 2205/332* (2013.01); *A61M 2205/3327* (2013.01);
(Continued)

(58) Field of Classification Search
CPC ............ A61M 25/1002; A61M 25/104; A61M 25/10; A61M 2205/332
See application file for complete search history.

(56) References Cited

U.S. PATENT DOCUMENTS 4,630,609 A * 12/1986 Chin ................... A61M 25/104
604/101.01
4,793,359 A    12/1988 Sharrow
(Continued)

FOREIGN PATENT DOCUMENTS

| EP | 0 347 023 A2 | 12/1989 |
| EP | 2 593 171 A2 | 5/2013 |
| WO | WO 2008/089424 | 7/2008 |

OTHER PUBLICATIONS

Partial European Search Report for European Application No. 19200456.2 dated Mar. 2, 2020 (12 pages).

*Primary Examiner* — Quynh-Nhu H. Vu
(74) *Attorney, Agent, or Firm* — Crowell & Moring LLP

(57) ABSTRACT

An expandable dilation member may include a proximally-tapered portion to dilate a stricture. The dilation member may be distally advanced in an unexpanded state over a wire guide through the stricture. The dilation member may then be configured in an expanded state, where the dilation member has a longitudinal profile that includes the proximally-tapered portion. A handle assembly proximally pulls the dilation member in the expanded state. In response, the proximally-tapered portion engages with and biases the stricture. When biasing the stricture, the proximally-tapered portion exerts a plurality of different types of forces, including a shearing force, a radial force, and in some procedures, a torsional force. In some embodiments, the proximally-tapered portion has a continuous taper from a smallest diameter to a largest diameter. In other embodiments, the proximally-tapered portion has at least one constant-diameter portion longitudinally disposed in between the smallest diameter and the largest diameter.

13 Claims, 15 Drawing Sheets

(52) U.S. Cl.
CPC .............. *A61M 2210/105* (2013.01); *A61M 2210/1057* (2013.01)

(56) References Cited

U.S. PATENT DOCUMENTS

| | | | |
|---|---|---|---|
| 4,832,691 A | | 5/1989 | Witzel |
| 5,078,725 A | * | 1/1992 | Enderle ................. A61M 29/02 |
| | | | 604/103.13 |
| 5,092,839 A | * | 3/1992 | Kipperman ......... A61M 25/104 |
| | | | 606/159 |
| 5,102,390 A | * | 4/1992 | Crittenden .......... A61M 25/104 |
| | | | 604/103.1 |
| 5,169,386 A | | 12/1992 | Becker et al. |
| 5,273,536 A | | 12/1993 | Savas |
| 5,338,298 A | * | 8/1994 | McIntyre .......... A61M 25/1002 |
| | | | 604/103.07 |
| 5,470,313 A | * | 11/1995 | Crocker ............ A61M 25/1034 |
| | | | 604/916 |
| 5,645,560 A | * | 7/1997 | Crocker ............ A61M 25/1029 |
| | | | 606/108 |
| 5,769,871 A | | 6/1998 | Mers Kelly et al. |
| 6,221,043 B1 | | 4/2001 | Fischell et al. |
| 6,290,485 B1 | * | 9/2001 | Wang ................ A61M 25/1029 |
| | | | 425/522 |
| 6,488,653 B1 | * | 12/2002 | Lombardo ........ A61M 25/1002 |
| | | | 604/103.06 |
| 6,835,189 B2 | * | 12/2004 | Musbach .......... A61M 25/1029 |
| | | | 604/916 |
| 7,303,798 B2 | | 12/2007 | Bavaro et al. |
| 7,479,120 B2 | | 1/2009 | Gregersen |
| 7,485,099 B2 | | 2/2009 | Benderev |
| 7,942,850 B2 | | 5/2011 | Levit et al. |
| 8,827,929 B2 | | 9/2014 | O'Dea |
| 8,873,900 B2 | * | 10/2014 | O'Beirne .......... A61M 25/104 |
| | | | 385/12 |
| 9,402,983 B1 | * | 8/2016 | Nath ................ A61M 25/1002 |
| 2001/0023335 A1 | | 9/2001 | Fischell et al. |
| 2002/0082553 A1 | | 6/2002 | Duchamp |
| 2008/0188803 A1 | | 8/2008 | Jang |
| 2017/0007810 A1 | * | 1/2017 | Parsons .................... A61F 2/95 |
| 2017/0042519 A1 | | 2/2017 | Sotak et al. |

* cited by examiner

DILATION PROCEDURES WITH EXPANDABLE DILATION DEVICES

CROSS-REFERENCE TO RELATED APPLICATIONS

The present application claims the benefit of U.S. Provisional Application No. 62/739,521, filed Oct. 1, 2018. The contents of U.S. Provisional Application No. 62/739,521 are hereby incorporated by reference in their entirety.

TECHNICAL FIELD

The present invention relates generally to medical devices, and more particularly to dilators.

BACKGROUND

Certain bodily or anatomical organs or other structures define a passageway for air, food, bodily fluids, waste, etc. to pass through. Such an anatomical structure may form or develop a stricture, which narrows the passageway, making the passage of whatever is intended to pass through it more difficult. For example, the esophagus may form a stricture, which may make swallowing more difficult. Benign esophageal strictures may form as a result of different causes, such esophageal resection due to Barrett's esophagus or cancer, radiation, or for congenital reasons.

One way to treat problems caused by a stricture is to reduce or eliminate the narrowing caused by the stricture through a dilation process. To perform dilation, a dilator applies a force to the tissue of the stricture that causes the tissue to stretch, and in turn widen the passageway. Desirably, the tissue stays in its stretched state as long as possible rather than return to its initial, narrowing state so that the passageway stays sufficiently open or patent for as long as possible.

One type of dilator is a bougie dilator. A physician can dilate a stricture using a bougie dilator by distally moving, such as by pushing, the bougie dilator through the restricted passageway. The bougie dilator may have a distal taper and so pushing the bougie dilator through the passageway may create an outward bias that stretches the stricture, which in turn widens the passageway. The pushing against the stricture may create a force feedback felt by the physician that indicates how much resistance to the distal movement the stricture is providing. The force feedback may be helpful to the physician in that it may indicate whether he/she can select a larger-sized bougie dilator and perform another dilation process to safely increase the size of the passageway, or to stop before undesirably causing a perforation in the tissue.

In addition to providing force feedback, a bougie dilator may be advantageous in that it imparts two forces, a radial force and a shearing force, on the tissue, which may cause the tissue to stay stretched, and in turn the passageway to stay sufficiently wide, for a longer period of time compared to if only one force caused the stretching. However, one disadvantage of the bougie dilator is that they are typically not wire guidable (i.e., not advanced over a wire guide to the treatment site), and thus unable to dilate small and/or tortuous strictures. Another disadvantage is that a pushing motion may generally be a less controlled motion than a pulling motion. However, a bougie dilator needs to dilate through pushing since its diameter is larger than the initial state of the stricture over at least some of the length of the bougie dilator.

Another type of dilator is a balloon dilator. A physician can dilate a stricture using a balloon dilator by moving the balloon dilator in its deflated state into a position within the stricture, and then inflating the balloon. As the balloon inflates, it biases the stricture with a radial force, causing the tissue to stretch. A balloon dilator may be advantageous since it is wire guidable, and thus may be more suitable for dilating smaller and/or tortuous strictures than a bougie dilator. However, a balloon dilator may be less advantageous than a bougie dilator in that it imparts only one force—a radial force—on the tissue, whereas a bougie dilator imparts both a shearing force and a radial force. Another disadvantage is that inflation of the balloon dilator through use of an inflation device does not provide the force feedback like the bougie dilator, and thus does not provide the helpful indication to the physician as to whether to stop the dilation or continue widening the passageway. Without receiving the force feedback, the physician may be unable to ascertain a compliance of the stricture. Tissue that is not very compliant, i.e., it is stiff, may provide a higher likelihood that the physician will dilate the balloon too much, causing the tissue to perforate. On the other hand, tissue that is very compliant may provide a higher likelihood that the physician does not dilate the stricture enough, increasing the likelihood that follow-up dilation therapy will be needed, and most likely sooner. New dilation procedures and devices to perform the dilation procedures may be desirable to overcome the aforementioned problems with existing dilation procedures.

BRIEF SUMMARY

The present description describes medical devices that include dilators and methods for dilating a stricture. In one embodiment, a method includes: proximally moving a proximally-tapered portion of a dilation member through a stricture of a bodily structure providing a passageway; and dilating the stricture with the proximally-tapered portion in response to proximally moving the proximally-tapered portion through the stricture.

In some embodiments, the proximally-tapered portion includes a plurality of stages, each of the plurality of stages has an associated length of constant diameter, and the stages have different constant diameters from each other over their respective lengths.

In some embodiments, a stage of the plurality of stages engages the stricture over a length of constant diameter associated with the stage in response to proximally moving the proximally-tapered portion through the stricture.

In some embodiments, a second stage engages the stricture over a second length of constant diameter associated with the second stage in response to proximally moving the proximally-tapered portion through the stricture, where the constant diameter over the second length is greater than the constant diameter over the first length.

In some embodiments, a proximal taper of a second stage engages the stricture in response to proximally moving the proximally-tapered region through the stricture; in response to the proximal taper engaging the stricture, the balloon deflates before the second stage engages the stricture over a second length of constant diameter associated with the second stage, and the dilation member is withdrawn from the bodily structure in response to deflating the dilation member.

In some embodiments, the proximally-tapered portion includes a continuously decreasing diameter of a length of the proximal portion in a proximal direction.

In some embodiments, the proximally-tapered portion has an angle relative to a central axis of the dilation member in a range of about 2 to about 6.5 degrees.

In some embodiments, a proximal end of the dilation member is positioned distally past a proximal end of the stricture by being distally advanced in an unexpanded state through the stricture until the proximal end of the dilation member is at a position distally past the proximal end of the stricture. Then, the dilation member changes from the unexpanded state to the expanded state.

In some embodiments, the dilation member rotates while the dilation member proximally moves through the stricture.

In some embodiments, a force gauge measures a resistance to the proximal movement of the dilation member provided by the stricture by measuring an amount of longitudinal force proximally moving the elongate member.

In some embodiments, at least one sensor attached to the dilation member sense an amount of elongation of the dilation member in response to proximal movement of the dilation member.

In another embodiment, a method includes: pulling a proximally-tapered portion of a dilation member through a stricture of a bodily passageway of a patient; and biasing the stricture with a shearing force and a radial force in response to pulling the proximally-tapered portion through the stricture.

In some embodiments, the proximally-tapered portion is rotated while pulled through the stricture, and the stricture is biased with a torsional force in response to the proximally-tapered portion rotating.

In some embodiments, the proximally-tapered portion includes a plurality of stages, where each of the plurality of stages has an associated length of constant diameter, where the stages have different constant diameters from each other over their respective lengths, and where a stage engages the stricture over a length of constant diameter associated with the stage in response to the proximally-tapered portion pulled through the stricture.

In some embodiments, a second stage engages the stricture over a second length of constant diameter associated with the second stage in response to the proximally-tapered portion pulled through the stricture, where the constant diameter over the second length is greater than the constant diameter over the first length.

In another embodiment, a method includes: proximally moving a longitudinal length of a dilation member through a stricture of a bodily structure, where the dilation member includes a plurality different diameters over the longitudinal length, and biasing the stricture with the dilation member over the plurality of different diameters in response to proximally moving the dilation member through the stricture.

In some embodiments, biasing the stricture with the dilation member over the plurality of different diameters includes biasing the stricture with the dilation member over the plurality of different diameters without deflating the dilation member.

In another embodiment, a dilation system includes: an elongate tubular member extending from a proximal portion to a distal portion, a handle assembly operatively coupled to the elongate tubular member, the handle assembly configured to proximally pull the elongate tubular member, and a dilation member disposed about the elongate tubular member at the distal portion. The dilation member, when in an expanded state, comprises a plurality of constant-diameter portions comprising a maximum diameter portion and a proximal portion proximal to the maximum diameter portion. The proximal portion has a smaller diameter than the maximum diameter portion. In addition, the dilation member does not have a diameter smaller than a diameter of the proximal diameter portion over a longitudinal length extending from the proximal portion to the maximum diameter portion.

In some embodiments, the proximal portion includes a proximal-most constant-diameter portion of a plurality of proximal portions proximal to the maximum diameter portion.

In another embodiment, a dilation system includes: an elongate tubular member extending from a proximal portion to a distal portion, a handle assembly operatively coupled to the elongate tubular member, the handle assembly configured to proximally pull the elongate tubular member, and a dilation member disposed about the elongate tubular member at the distal portion, where the dilation member, when in an expanded state, includes a proximally-tapered portion that includes an angle relative to a central axis of the dilation member in a range of about 2.5 degrees to about 6.5 degrees, and a longitudinal length over the proximally-tapered portion is in a range of about 25 mm to about 230 mm.

In some embodiments, a maximum diameter of the proximally-tapered portion is in a range of about 8 mm to about 20 mm.

In some embodiments, the handle assembly is configured to axially rotate the elongate tubular member.

In some embodiments, a force gauge is configured to measure an amount of pulling force that the handle assembly is exerting on the tubular member.

In some embodiments, a sensor is configured to sense an amount of elongation of the dilation member in response to the handle assembly proximally pulling the elongate tubular member.

In some embodiments, the dilation member includes a dilation balloon.

In some embodiments, the bodily structure includes an esophagus of the patient.

In some embodiments, the bodily structure includes a pyloric sphincter.

Other embodiments are possible, and each of the embodiments can be used alone or together in combination. Accordingly, various embodiments will now be described with reference to the attached drawings.

DETAILED DESCRIPTION

The present description describes dilators and methods for dilating a stricture by proximally pulling the dilator through the stricture, receiving a force feedback in response to the proximally pulling, and biasing the stricture with at least two of a radial force, a shearing force, or a torsional force in response to the proximal pulling. The dilator may be wire guidable, and thus suitable for dilating relatively small and/or tortuous strictures, may reduce risks of perforating tissue and/or reduce the frequency of follow up procedures by providing force feedback and biasing the stricture with two or more different forces, and may provide a more controlled dilation through pulling instead of pushing. These and other dilation features and advantages are explained in further detail below.

Figure 1:
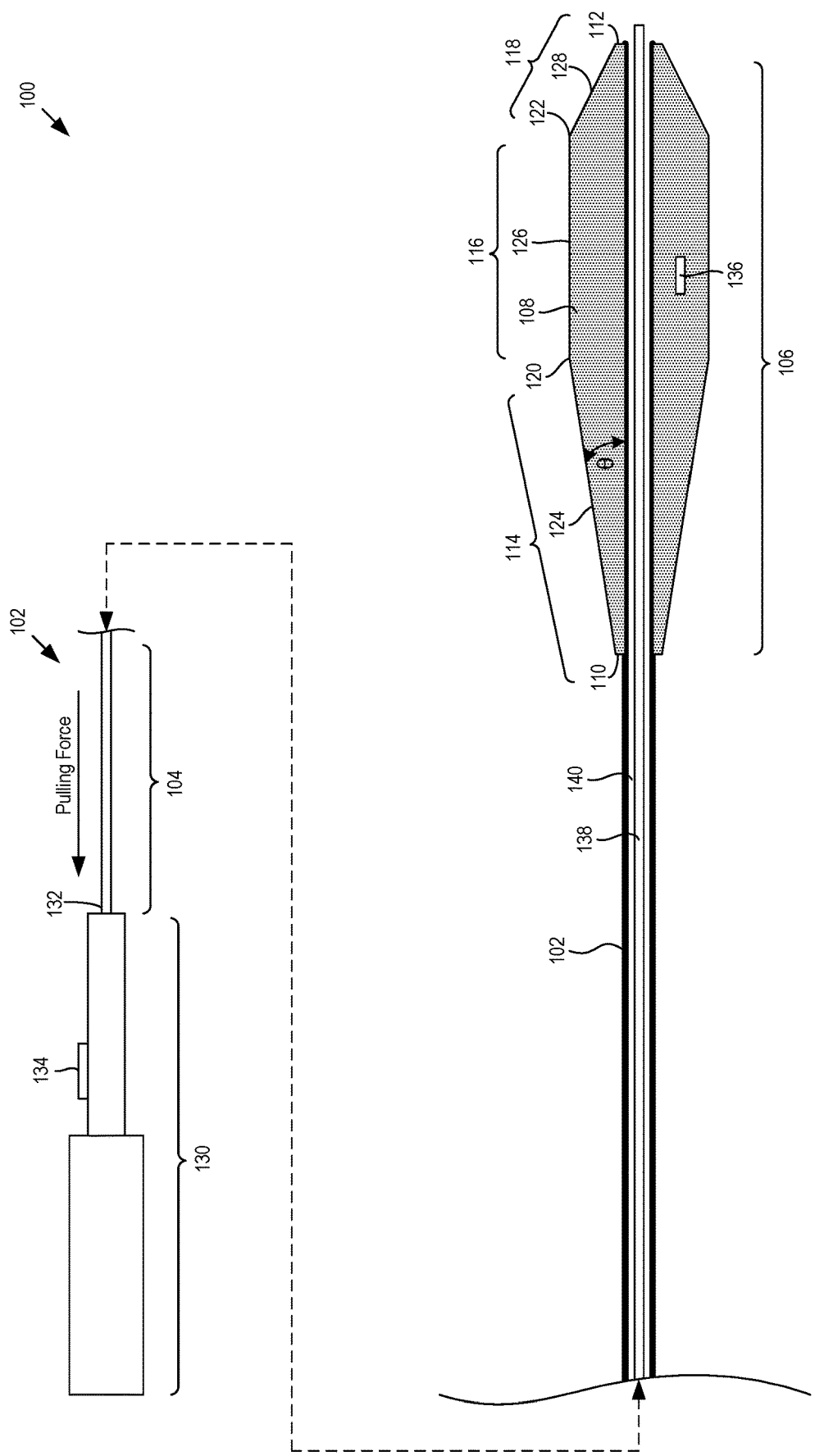
FIG. 1 shows a cross-sectional side view of an example dilation device.

FIG. 1 shows a cross-sectional side view of a first example dilator (or dilation device) 100. The dilator 100 includes an elongate tubular member (e.g., a catheter) 102 longitudinally extending from a proximal portion 104 to a distal portion 106. The dilator 100 may also include an elongate dilation member 108 disposed about and/or mounted on an outer surface of the tubular member 102 at the distal portion 106.

As described in further detail below, the dilation member 108 may be an expandable member that is configurable in an expanded state and in an unexpanded state. FIG. 1 shows the dilation member 108 in the expanded state. In general, the dilation member 108 may have a longitudinal length extending from a proximal end 110 to a distal end 112. Over at least a portion, such as substantially most, of the longitudinal length, the axial cross-section of the dilation member 108 expands to move from the unexpanded state to the expanded state, and contracts to move from expanded state to the unexpanded state. Accordingly, at a given point over the longitudinal length, the dilation member 108 may have an associated outer diameter. At the given point, the outer diameter may be larger when the dilation member 108 is in the expanded state than when in the unexpanded state. Otherwise stated, at the given point, the outer diameter increases as the dilation member 108 expands and moves from the unexpanded state to the expanded state, and decreases as the dilation member 108 contracts and moves from the expanded state to the unexpanded state In some example configurations, the expandable dilation member 108 may be a balloon, such as a dilation balloon. In addition or alternatively, the dilation member 108 may be made of a noncompliant material, such as polyethylene terephthalate (PET), or other relatively rigid material. Other configurations for the dilation member 108 may be possible.

In addition, when the dilation member 108 is in the expanded state, the dilation member 108 may have a longitudinal cross-sectional profile extending from the proximal end 110 to the distal end 112, as shown in FIG. 1. Along the longitudinal length, the dilation member 108 may include three portions, as defined or determined by its longitudinal cross-sectional profile, including a proximally-tapered portion 114, a constant diameter portion 116, and a distally-tapered portion 118. The constant-diameter portion 116 is disposed in between the proximally-tapered portion 114 and the distally-tapered portion 118. In addition, each portion may have an associated longitudinal length that forms a part of the total longitudinal length of the dilation member 108. In particular, the proximally-tapered portion 114 may have an associated longitudinal length extending from the proximal end 110 to a first intermediate point 120 where the proximally-tapered portion 114 and the constant-diameter portion 116 meet or connect to each other.

The longitudinal length of the proximally-tapered portion 114 may be suitable for dilating a certain stricture within a patient. For dilation members configured to dilate esophageal strictures, the proximally-tapered portion 114 may have a longitudinal length in a range of about 25 millimeters (mm) (about 1 inch) to about 230 mm (about 9 inches). Other lengths may be possible depending on the type of bodily structure having the stricture and/or being dilated, or the type of patient (e.g., adult human, infant, (non-human) animal, etc.) subjected to the dilation procedure.

The distally-tapered portion 118 may also have an associated longitudinal length, extending from the distal end 112 to a second intermediate point where the distally-tapered portion 118 and the constant-diameter portion 116 meet or connect to each other. The longitudinal length of the distally-tapered portion 118 may be different than the longitudinal length of the proximally-tapered portion 114, and in at least some embodiments much smaller than (such as less than half) the length of the proximally-tapered portion 114, since the distally-tapered portion 118 is not used to dilate the stricture and so does not need as long of a length as the proximally-tapered portion 114.

In addition, the constant-diameter portion 116 may have an associated longitudinal length extending from the first intermediate point 120 to the second intermediate point 122. The constant-diameter portion 116 may also have an associated diameter. In some embodiments, such as those used to dilate esophageal strictures, the diameter of the constant-diameter portion 116 may be in a range of about 8 mm to about 20 mm. Other diameters for the constant-diameter portion 116 may be possible, depending on the type of bodily stricture having the stricture and/or being dilated, or the type of patient.

In addition, each of the portions 114, 116, 118 may be defined by a portion of the outer surface of the dilation member 108 that extends over the associated longitudinal length of the respective portion. Accordingly, the outer surface of the dilation member 108 may include a proximally-tapered outer surface portion 124, a constant-diameter outer surface portion 126, and a distally-tapered outer surface portion 128.

The proximally-tapered outer surface portion 124 proximally tapers over an associated longitudinal length of the proximally-tapered portion 114, from the first intermediate point 120 to the proximal end 110. The outer diameter of the proximally-tapered portion 114, as determined or measured by the proximally-tapered outer surface portion 124, may generally decrease over the associated longitudinal length, from the first intermediate point 120 to the proximal end 110. In the particular example configuration shown in FIG. 1, the proximally-tapered portion 114 continuously tapers—i.e., has a continuously decreasing diameter—in the proximal direction over a length of the proximally-tapered portion 114 from the first intermediate point 120 to the proximal end 110.

The distally-tapered outer surface portion 128 distally tapers over an associated longitudinal length of the distally-tapered portion 118, from the second intermediate point 122 to the distal end 112. The outer diameter of the distally-tapered portion 118, as determined or measured by the distally-tapered outer surface portion 128, may generally decrease over the associated longitudinal length, from the second intermediate point 122 to the distal end 112.

The constant-diameter outer surface portion 126 longitudinally extends generally parallel with the elongate tubular member over an associated longitudinal length of the constant-diameter portion 116, from the first intermediate point 120 to the second intermediate point 122. The outer diameter of the constant-diameter portion 116, as determined or measured by the constant-diameter outer surface portion 126, may be generally or substantially constant over the associated longitudinal length, from the first intermediate point 120 to the second intermediate point 122.

In addition, in the example configuration shown in FIG. 1, the proximally-tapered portion 114 may have a relatively long proximal taper that allows the dilation member 108 to increasingly dilate the stricture at a desired rate. In some example configurations, the taper may form an angle θ with the tubular member 102 of about 2 to about 6.5 degrees. In some example configurations, the relatively long length of the of the proximally-tapered portion 114 may yield a longitudinal profile where the proximally-tapered portion 114 has an associated longitudinal length that is longer than the longitudinal length of the distally-tapered portion 118, as is the configuration shown in FIG. 1.

The dilator 100 may further include a handle assembly 130 coupled to a proximal end 132 of the elongate tubular member 102. The handle assembly 130 may be configured to control movement, including longitudinal and/or rotational movement, of the elongate tubular member 102 and/or the dilation member 108. As described in further detail below, the handle assembly 130 may be configured to exert a proximally longitudinal or pulling force on the elongate tubular member 102, such as at or near the proximal end 132, which in turn proximally moves the elongate tubular member 102 and the dilation member 108. Also as described in further detail below, the handle assembly 130 may be configured to exert an axial rotational force on the tubular member 102, which in turn causes the tubular member 102 and the dilation member 108 to rotate, such as axially rotate, about a central longitudinal axis of the tubular member 102 and the dilation member 108.

In some example configurations, the dilator 100 may include and/or be implemented with one or more measuring devices configured to measure an amount of resistance to the proximal movement. For at least some of these example configurations, the handle assembly 130 may include a force gauge 134 that is configured to measure an amount of proximally longitudinal or pulling force that the handle assembly 130 is exerting on the tubular member 102 to proximally move or pull the dilator 108 through the stricture. The amount of longitudinal or pulling force may be equal to or correspond to the resistance that the stricture is providing to the proximal movement of the dilation member 108. The force gauge 134 may include or be coupled to a display, such as a digital read-out, that a physician or other person can view to ascertain the amount of pulling force the handle assembly 130 is exerting on the tubular member 102 and/or the amount of resistance to the proximal movement provided by the stricture. In addition or alternatively, the dilator 100 may include one or more sensors 136 disposed on the outer surface of the dilation member 108, and configured to sense an amount of elongation of the dilation member 108 in response to the handle assembly 130 proximally pulling the dilation member 108 through the stricture. For clarity, wires and/or other circuitry used to communicate an electrical signal carrying information of the sensing to the handle assembly 130 and/or convert the information to elongation amount are not shown. The amount of elongation, may in turn, indicate the amount of resistance to the proximal movement provided by the stricture. For example, the force gauge 134 be connected to the sensor(s) 136 and receive and electrical signal from the sensor(2) 136 indicating an amount of elongation. The force gauge 134 may be configured to convert, such as by being configured with an algorithm, a lookup table, a function, or some other conversion mechanism, that can convert the indicated amount of elongation to an amount of pulling force the handle assembly 130 is exerting on the tubular member 102 and/or an amount of resistance to the proximal movement provided by the stricture. Although the example configuration in FIG. 1 shows the dilator 100 as including both a force gauge 134 and elongation sensor(s) 136, other example configurations of the dilator 100 may include only the force gauge 134. In still other example configurations, a force gauge 134 may not be included, and the operator relies solely on feel to gauge the amount of force feedback and/or resistance.

In addition, the dilator 100 may include or be configured to engage with an elongate wire guide 138 longitudinally extending at least a length of the elongate tubular member 102. In general, the wire guide 138 may have an outer diameter that is smaller than an inner diameter of a wire guide lumen 140 longitudinally extending through a body of the elongate tubular member 102. As described in further detail below, to perform a dilation procedure or process, a distal portion of the wire guide 138 may be distally advanced into a patient and to a treatment site where the stricture is located first, before the dilation member 108. The elongate tubular member 102 may be positioned over or about the wire guide 138, such as by positioning the elongate tubular member 102 so that the wire guide 138 is disposed within the wire guide lumen 140. The tubular member 102 and the dilation member 108 may then be distally advanced about or over the wire guide 138 to the treatment site. Utilization of the wire guide 138 may allow the dilation member 108 to navigate through relatively small strictures, compared to if it were distally advanced without the guidance provided by the wire guide 138.

FIGS. 2A-2G illustrate various stages of an example dilation process or procedure that may be performed with the example dilator 100 shown in FIG. 1. The dilation process is performed to dilate (i.e., make more patent) a passageway 142 that is being undesirably narrowed by a stricture 144 of a bodily or anatomical structure 146 of a patient. Example bodily structures may include an esophagus or a pyloric sphincter, although other bodily structures may be possible. A treatment site 148 within the patient may generally include an area of the patient that includes the stricture 144, the passageway 142 being narrowed by the stricture 144, and areas near or adjacent to the stricture 144 and passageway 142 where the distal portion 106 of the tubular member 102 and the dilation member 108 may be distally moved to in order to perform the dilation process.

Figure 2A:
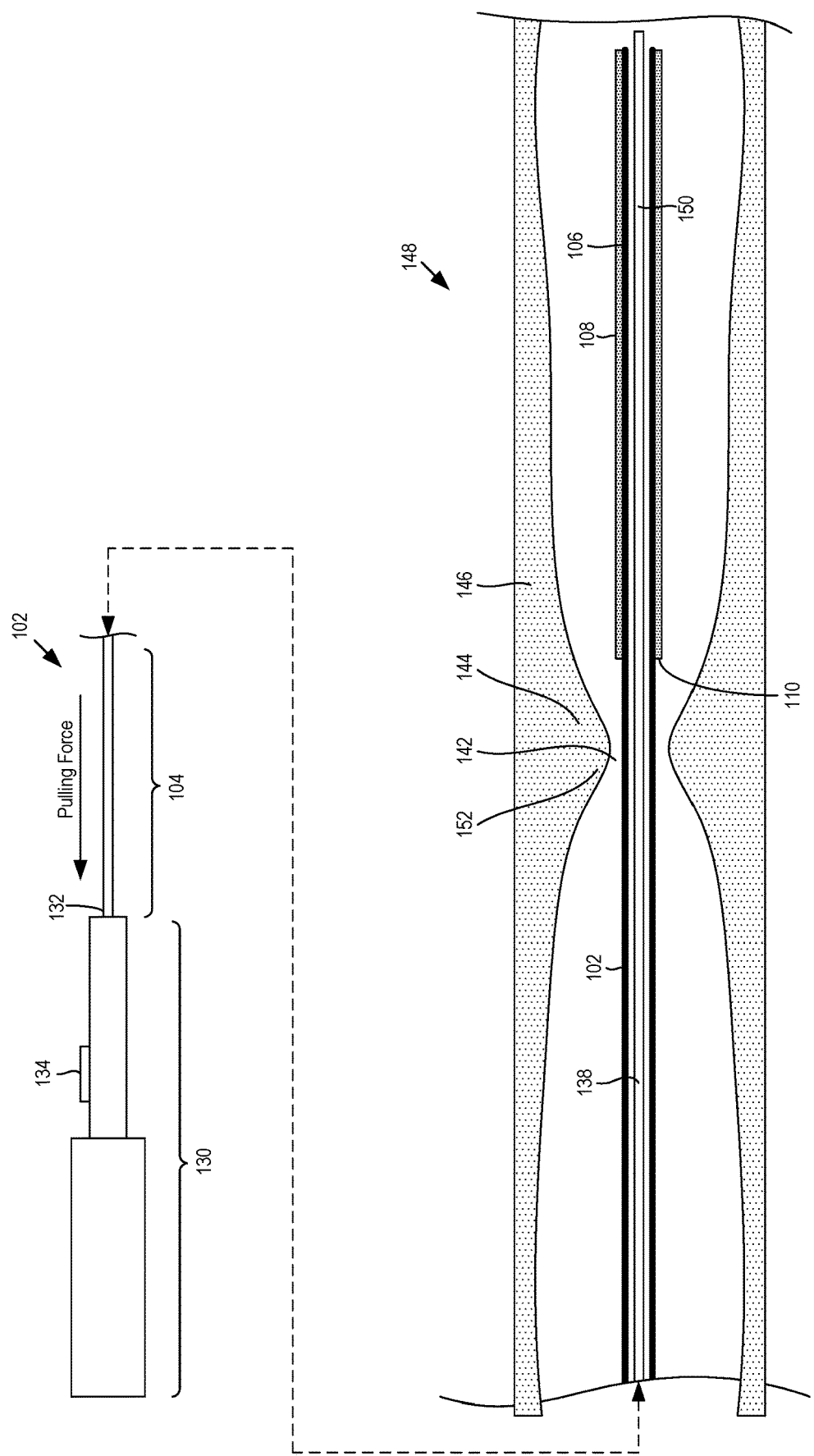
FIG. 2A shows a cross-sectional side view of a distal portion of an elongate member and a dilation member of the dilation device of FIG. 1 positioned distally past a stricture, where the dilation member is configured in an unexpanded state.

Referring to FIG. 2A, as an initial step of the dilation process, a distal portion 150 of the wire guide 138 may be distally advanced from outside of the patient to the treatment site 148. In particular, the distal portion 150 may distally advanced through the stricture 144 or the passageway 142 narrowed by the stricture 144 so that the distal portion 150 is distally past the stricture 144. Herein, reference to an object, such as the tubular member 102, the dilation member 108, or the wire guide 138, being moved through the stricture 144 may be used interchangeably with and/or mean the same as the object being moved through the passageway 142 narrowed by the stricture 144. As previously mentioned, use of the wire guide 138 may allow the dilation member 108 to move through smaller-sized passageways 142 and/or passageways 142 that are relatively more narrowed or restricted by given strictures.

Still referring to FIG. 2A, after the distal portion 150 of the wire guide 138 is at a desired position distally past the stricture 144, the tubular member 102 and the dilation member 108 may be distally advanced over or about the wire guide 138 to the treatment site 148. As shown in FIG. 2A, the dilation member 108 may be distally advanced to the treatment site 148 in its unexpanded or contracted state. By being in its unexpanded state, the dilation member 108 has a small enough outer diameter over its longitudinal length so that the dilation member 108 can be distally moved through the stricture 144. The distal portion 106 of the tubular member 102 and the dilation member 108 may be distally advanced through the stricture 144 until the proximal end 110 of the dilation member 108 is at a desired location distally past a proximal end 152 of the stricture 144. In some example methods, the desired position may be completely distally past the stricture 144. In other example methods, the desired position may not be completely distally past the stricture 144, but within the passageway 142 defined or circumferentially surrounded by the stricture 144.

Figure 2B:
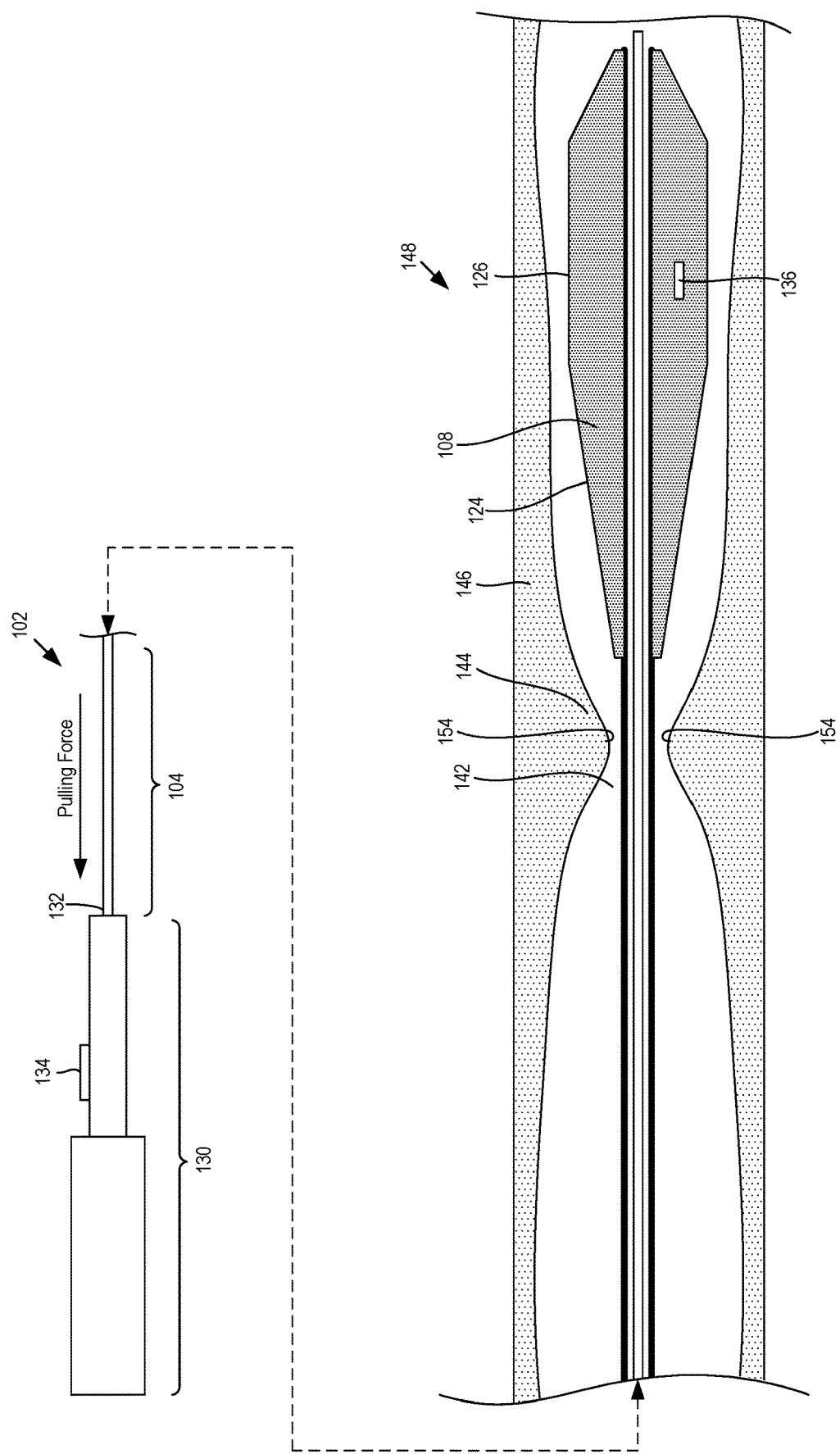
FIG. 2B shows a cross-sectional side view of the distal portion and the dilation member positioned distally past the stricture as in FIG. 2A, but with the dilation member configured in an expanded state.

Referring to FIG. 2B, when the dilation member 108 is in the desired position, the dilation member 108 may be moved or expanded from the unexpanded state to the expanded state. In some example methods, fluid and/or a gas (e.g., air) may be injected into a cavity of the dilation member 108, causing the dilation member 108 to expand. Depending on the desired position, the size of the stricture 144, and/or the outer diameter of the dilation member 108 in its expanded state, when the dilation member 108 is initially configured in the expanded state, none of the outer surface of the dilation member 108 may contact and/or bias an inner wall 154 of the stricture 144, or alternatively, at least a portion of the proximally-tapered outer surface 124 and/or at least a portion of the constant-diameter outer surface 126 may contact and/or bias the inner wall 154 of the stricture 144.

Figure 2C:
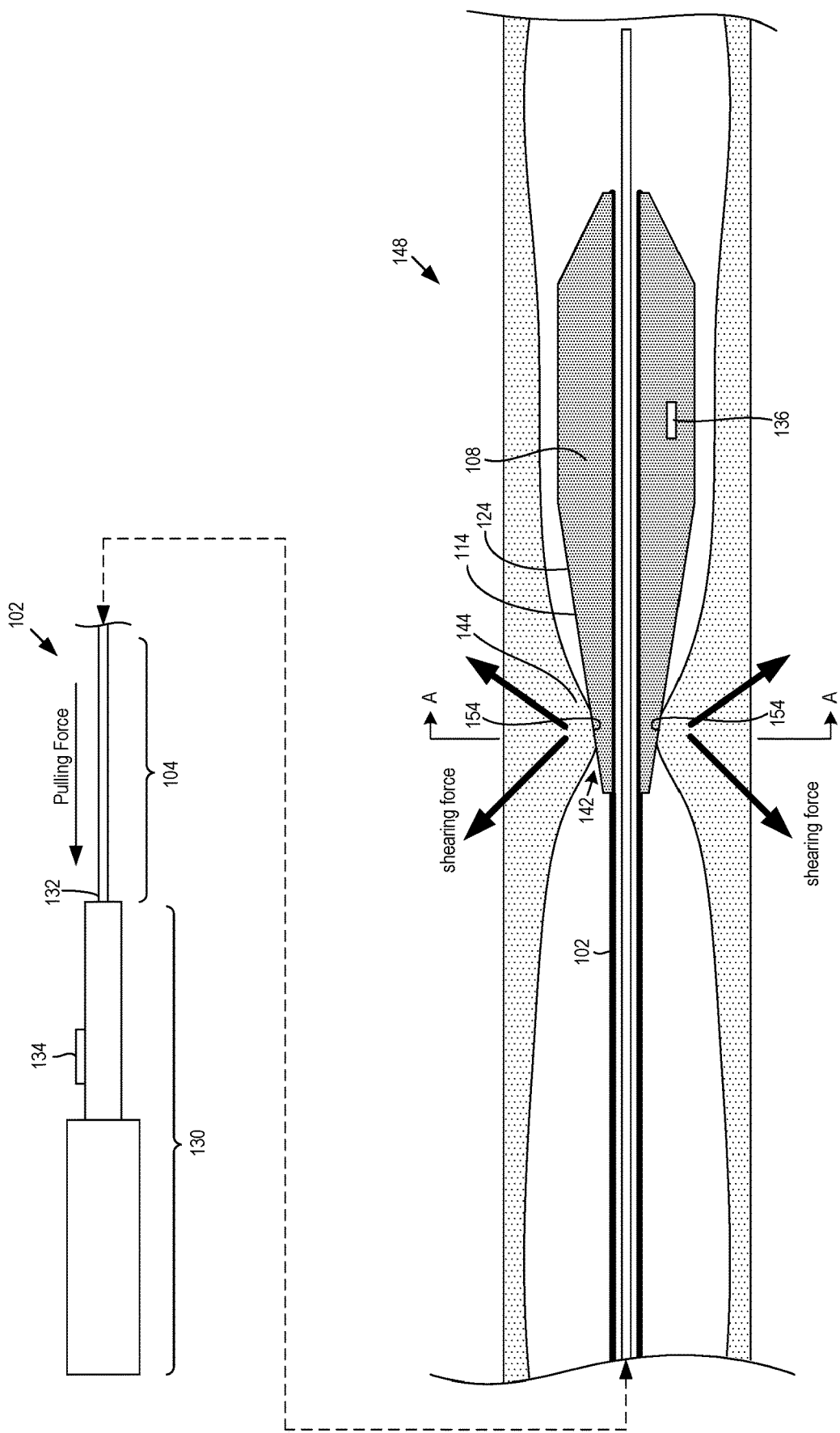
FIG. 2C shows a cross-sectional side view of a proximally-tapered portion of the dilation member in the expanded state engaging with and dilating the stricture by exerting a shearing force on the stricture.

Referring to FIG. 2C, upon being configured in its expanded state, the handle assembly 130 may pull or longitudinally exert a force in a proximal direction on the proximal end 132 of the tubular member 102 to proximally move the proximally-tapered portion 114 of the dilation member 108 through the stricture 144. In response to the proximal movement, the proximally-tapered portion 114 may begin dilating the stricture 144. Since the proximally-tapered portion 114 has a plurality of different diameters (e.g., continuously increasing diameters in a distal direction) over a longitudinal length of the proximally-tapered portion 114, the proximally-tapered portion 118 may dilate the stricture 144 over the plurality of different diameters in response to proximally moving through the stricture 144. As described in further detail below, the proximally-tapered portion 114 may bias the stricture 144 over the plurality of different diameters in response to the proximal movement and during a period of time during which the dilation member 108 remains in its expanded (e.g., inflated) state. That is, the proximally-tapered portion 114 dilates the stricture 144 by biasing the stricture 144 over the plurality of different diameters in response to the proximal movement and without being deflated.

The proximally-tapered portion 114, or more generally the dilation member 108, may dilate the stricture 144 by exerting or imparting one or more forces on the inner wall 154 of the stricture 144. The one or more forces exerted on the inner wall 154 may cause tissue, which may include muscle fibers, of the stricture 144 to stretch, and in turn widen the passageway 142. An aim of the dilation, including the biasing of the stricture 144 with the one or more forces, is to stretch the tissue so that it stays in its stretched state when the dilation member 108 is removed from the patient and no longer biasing the stricture 144, as opposed to the tissue returning to its original form and undesirably narrowing the passageway 142.

Figure 2D:
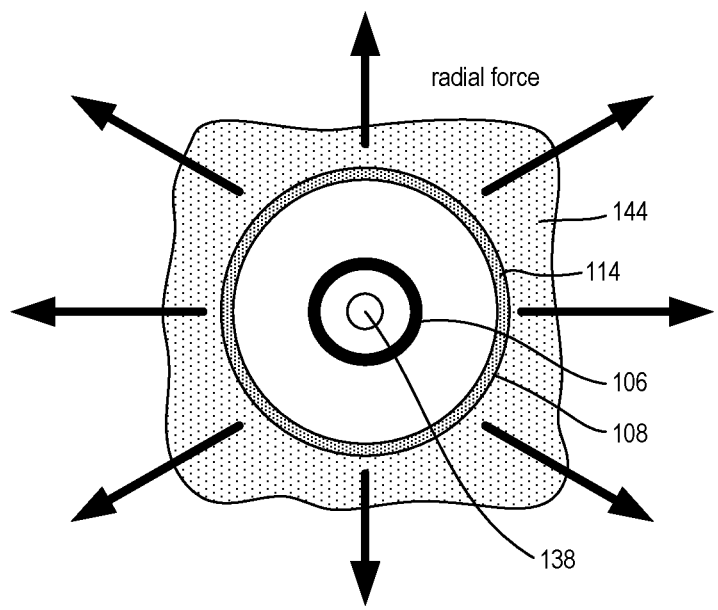
FIG. 2D shows a cross-sectional axial view of the dilation member taken along line A-A of FIG. 2C, illustrating the proximally-tapered portion of FIG. 2C exerting a radial force on the stricture.

Referring both to FIGS. 2C and 2D, the proximally pulling of the dilation member 108, and in turn proximal movement of the proximally-tapered portion 114 through the stricture 144 may cause the proximally-tapered portion 114 to bias the stricture 144 with both a shearing force (indicated in FIG. 2C) and a radial force (indicated in FIG. 2D). Referring particularly to FIG. 2C, a shearing force imparted on the stricture 144 includes a plurality of unaligned forces created by proximal movement of the proximally-tapered portion 114 through the stricture 144 and the biasing of the proximally-tapered portion 114 on the stricture 144 in response to the proximal movement. The unaligned forces created by the proximal movement and the biasing may bias the tissue in different, opposite directions, which in turn may longitudinally stretch all or at least some of the tissue of the stricture 144. Tissue of the stricture 144, including muscle fibers, that extends in a longitudinal direction may be especially or be the most significantly affected by the shearing forces.

Referring particularly to FIG. 2D, radial forces imparted on the stricture 144 include those forces extending radially outward from a central longitudinal axis of the dilation member 108. The radial forces may also be created by the proximal movement of the proximally-tapered portion 114 through the stricture 144 and the biasing of the proximally-tapered portion 114 on the stricture in response to the proximal movement. The radial forces may radially stretch all or at least some of the tissue of the stricture 144. Tissue of the stricture 144, including muscle fibers, that extends in a circular direction around the dilation member 108 during dilation may be especially or be the most significantly affected by the radial forces.

Figure 2E:
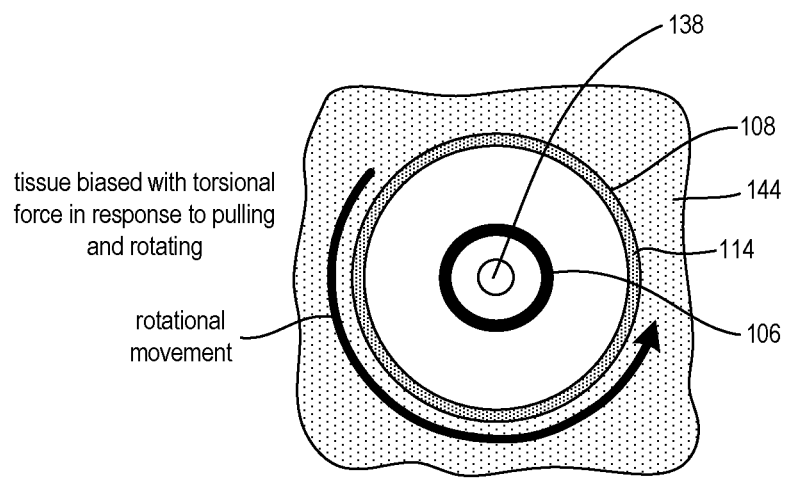
FIG. 2E shows another cross-sectional axial view of the dilation member taken along line A-A of FIG. 2C, illustrating the proximally-tapered portion of FIG. 2C exerting a torsional force on the stricture as the dilation member is being axially rotated.

Referring also to FIG. 2E, in some example methods, the handle assembly 130 may exert a rotational force on the tubular member 102, causing the tubular member 102 and the dilation member 108 to rotate, such as axially rotate, about a central longitudinal axis. As the dilation member 108 rotates while engaging or biasing the stricture 144, the dilation member 108 may bias the stricture 144 with a rotational or torsional force. The torsional force may provide an additional way to stretch the tissue of the stricture 144 to dilate the passageway. The handle assembly 130 may exert the rotational force simultaneously with the pulling force so that the dilation member 108 rotates while it proximally moves through the stricture 144. Accordingly, when the dilation member 108 axially rotates while proximally moving (being pulled) through the stricture 144, the dilation member 108 may simultaneously exert three forces on the stricture 144, including a shearing force, a radial force, and a torsional force. In some example configurations, the tubular member 102 may be configured with a braid or as a braided stricture, which may be suitable or optimal for being subjected to a rotational force.

Referring particularly to FIG. 2C, as the proximally-tapered portion 114 proximally moves through the stricture 144, a given cross-section of the stricture 144 is continuously biased with increasingly larger cross-sections (i.e., cross-sections with increasingly larger diameters) of the proximally-tapered portion 114. In response, the tissue of the given cross-section will continuously stretch and expand, widening the passageway 142.

In at least some example methods, the handle assembly 130 proximally pulls the tubular member 102 and the dilation member 108 in response to movement of the operator of the handle assembly 130. For example, the operator, who is holding the handle assembly 130 during the dilation procedure, moves the handle assembly 130 in a proximal direction—i.e., pulls the handle assembly 130—to cause the tubular member 102 and the dilation member 108 to proximally move through the stricture 144. As the dilation member 108 biases the stricture 144, the equal and opposite force that the stricture 144 exerts on the dilation member 108 provides a resistance or resistive force to the proximal pulling. Accordingly, as the operator proximally pulls the handle assembly 130, the resistance to the proximal pulling that the stricture 144 creates provides a force feedback to the operator. That is, as a force feedback, the resistance to the proximal movement is fed back to the operator by way of the handle assembly 130 to give an indication to the operator how much proximal force is needed to pull the dilation member 108 through the stricture 144.

As the operator proximally pulls the handle assembly 130, the operator may use the force feedback to determine whether to keep pulling or to stop. If the dilation member 108 exerts too much force on the stricture 144 and/or causes the tissue of the stricture 144 to stretch too much, the tissue can tear or perforate, which is undesirable. In at least some example methods, as the dilation member 108 proximally moves through the stricture 144, more and more surface area of the proximally-tapered outer surface 124 will contact and bias the stricture 144, including those sections with the larger outer diameters, which in turn causes increasingly larger amounts of the stricture 144 to be biased and stretched, and also increasingly larger amounts of the stricture 144 to be displaced or moved from their original positions by increasingly greater amounts. This, in turn, may provide a resistance in the form of force feedback that continuously increases as the operator continuously pulls the handle assembly 130 and the proximally-tapered portion 114 continuously moves through and biases the stricture 144.

As the resistance or force feedback continues to increase, the operator may sense, through his/her feel of the force feedback, whether to continue pulling or to stop. For example, in response to the continuous force feedback, if the operator determines that the stricture 144 is providing too much resistance—i.e., that the operator has to pull with too much force to have the dilation member 108 continue to move through the stricture 144—the operator may determine to stop pulling, since the force feedback gives an indication that a high likelihood of the tissue perforating exists if the operator continues to pull. In the event that the operator determines to stop pulling, the dilation member 108 may be deflated or moved into its unexpanded state before all of the dilation member 108 has been proximally moved through the stricture 144, and the dilation member 108 in the unexpanded state and the distal portion 106 of the tubular member 102 may be proximally withdrawn through the stricture 144 to outside of the patient. Alternatively, as long as the operator determines that the stricture 144 is not providing too much resistance, the operator may determine to continue pulling, and in turn continue to move the dilation member 108 through the stricture 144 and increasingly widen the passageway 142.

In addition or alternatively, in at least some example dilation procedures, as the dilation member 108 proximally moves through the stricture 144, the force feedback may be constantly or continuously measured by the force gauge 134. An output device coupled to or included with the force gauge 134 may provide an output of or associated with the measured force feedback. For example, the output device may provide a digital read-out of the measured force, which the operator may monitor or observe to determine whether to continue dilating the stricture 144. In addition or alternatively, the force gauge 134 and/or the output device may be configured to continuously compare the force feedback with a force threshold value. The force threshold value may be a predetermined force value associated with a resistive force that has a relatively high degree of causing tissue perforation. In the event that the measured force feedback is within a predetermine range of, reaches, or exceeds the force threshold value, the output device may be configured to output a warning (e.g., audibly, visually, and/or tactile), which may indicate to the operator to stop proximal movement of the dilation member 108 and/or further dilation of the stricture 144.

Figure 2F:
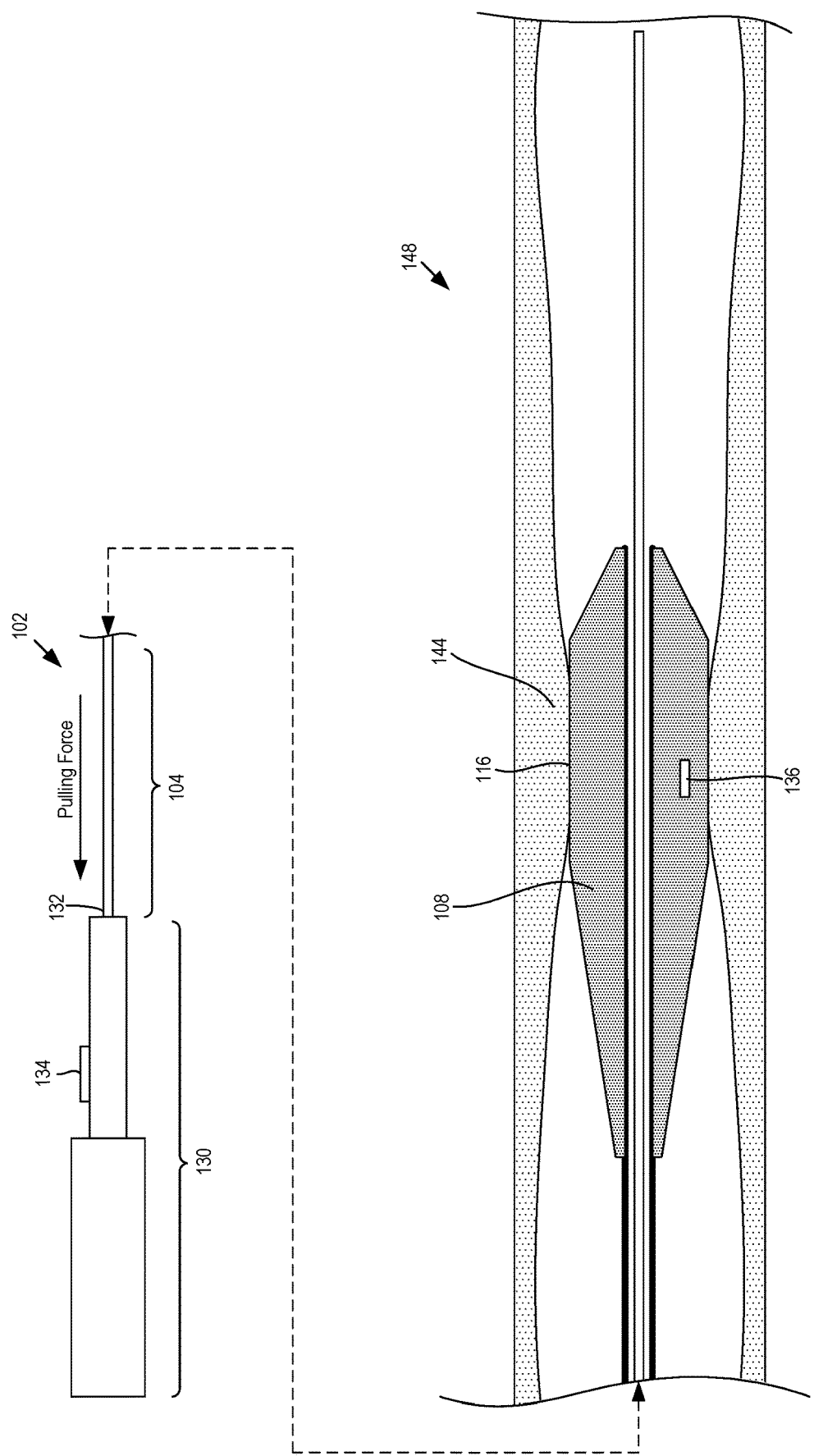
FIG. 2F shows a cross-sectional side view of a constant-diameter portion of the dilation member engaging with the stricture.
Figure 2G:
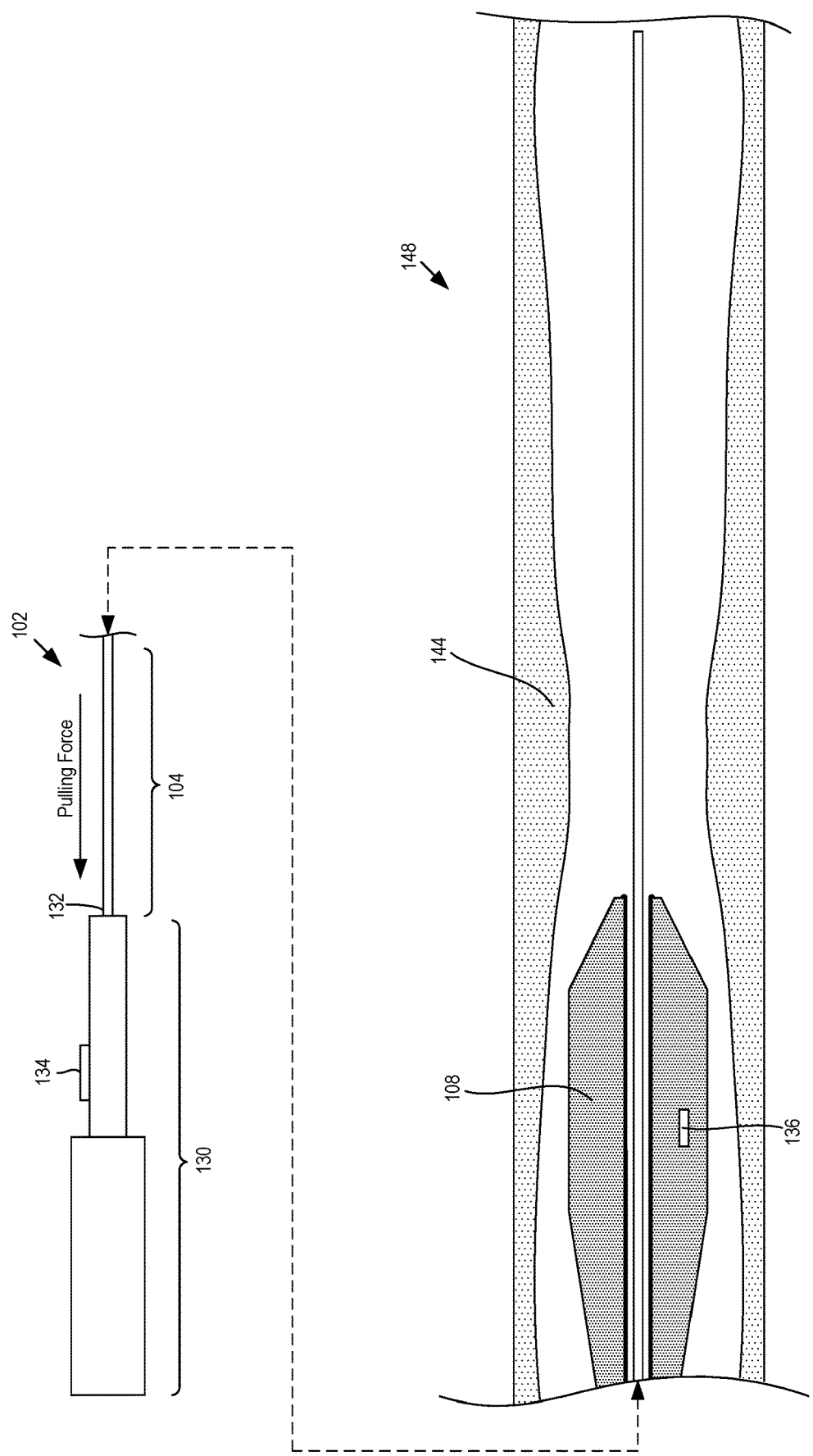
FIG. 2G shows a cross-sectional side view of the dilation member being completely proximally moved through the stricture while in the expanded state.

Referring to FIG. 2F, if the dilation member 108 continues to be proximally moved through the stricture 144, the constant-diameter portion 116 may come into contact with the stricture 144. The constant-diameter portion 116 may be the portion of the dilation member 108 that has the largest outer diameter, and so when a given section of the stricture 144 comes into contact with the constant-diameter portion 116, it will have been stretched to its maximum by the dilation member 108. In at least some example dilation procedures, when the constant-diameter portion 116 comes into contact with the stricture 144, the stricture 144 may still provide some contraction around the constant-diameter portion 108, and in turn provide some resistance to the proximal movement of the dilation member 108. Since the constant-diameter portion 108 does not change diameter, then the resistance may be relatively constant, rather than constantly changing. During the time that the operator is pulling the constant-diameter portion 116 through the stricture 144, the resistance to the proximal movement may provide a relatively constant amount of force feedback to the operator, during which time the operator may determine whether to perform a subsequent dilation procedure using a larger dilation member, such as one where the constant-diameter portion has a larger outer diameter and/or the proximally-tapered portion distally increases to a larger outer diameter compared to the one used in the current dilation procedure. Referring to FIG. 2G, if the operator determines to continue pulling, the dilation member 108 may be completely moved through the stricture 144, until it is completely proximally past the stricture 144, leaving the stricture 144 in a stretched or dilated state. Accordingly, the dilation member 108 may have been completely, proximally moved through the stricture 144 to bias the stricture 144 over different diameters while remaining in its expanded state, and/or without being deflated.

Figure 3:
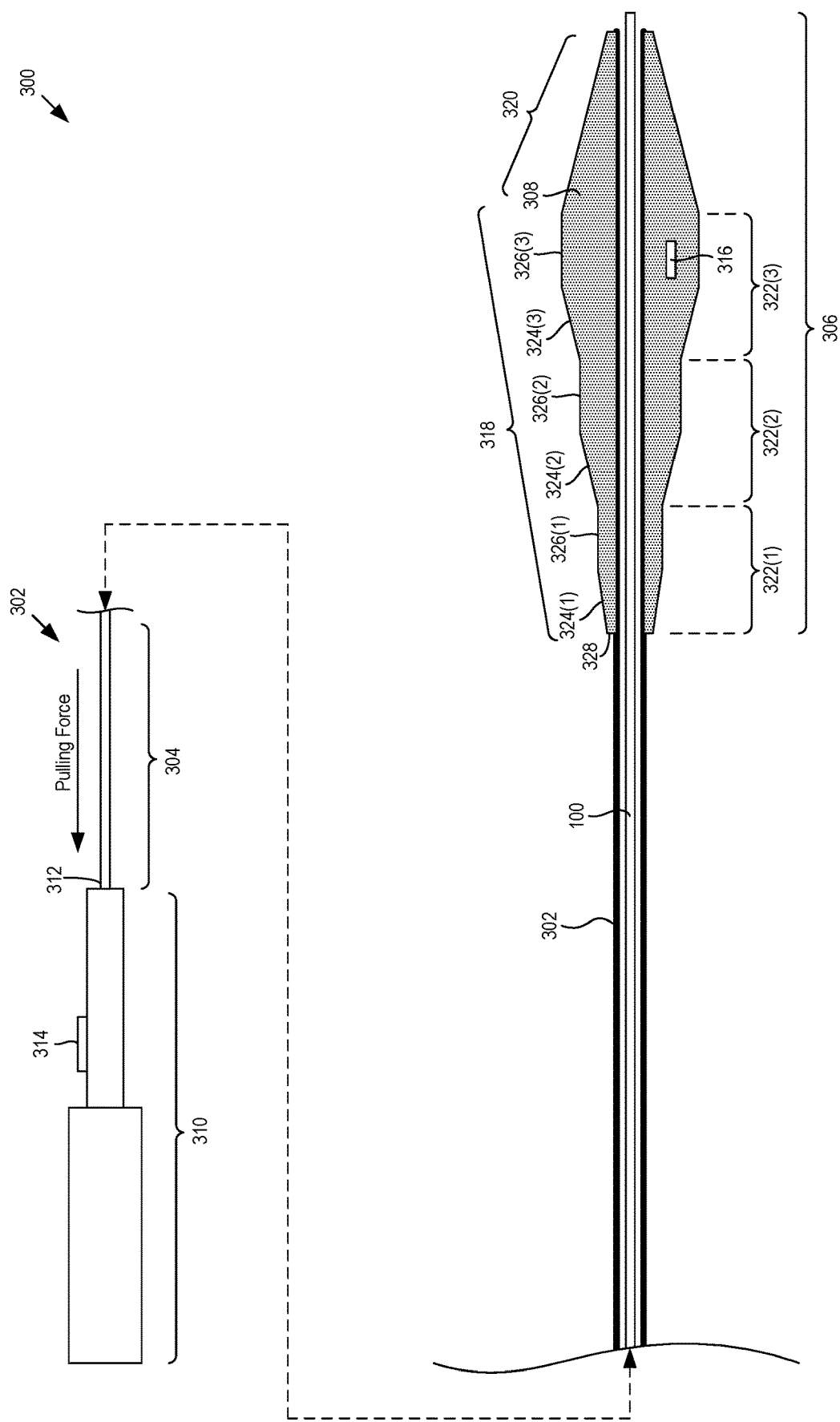
FIG. 3 shows a cross-sectional side view of another example dilation device.

FIG. 3 shows another example dilator 300 that may be used to perform a dilation process. The example dilator 300 is similar to the example dilator 100 shown and described with reference to FIGS. 1-2G, in that the example dilator 300 includes an elongate tubular member (e.g., a catheter) 302 extending from a proximal portion 304 to a distal portion 306, and a dilation member 308 disposed and/or mounted on an outer surface of the tubular member 302 at the distal portion 306. In addition, a handle assembly 310 may be coupled to a proximal end 312 of the tubular member 302. The handle assembly 310 of FIG. 3 may be configured to operate in the same or similar way as the handle assembly 130 shown and described with reference to FIGS. 1-2G in that the handle assembly 310 may be configured exert a proximally pulling force on the tubular member 302 to proximally pull the tubular member 302 and the dilation member 308. Additionally, in some example configurations, the handle assembly 310 may be configured to axially rotate the tubular member 302 to axially rotate the dilation member 302 about a central longitudinal axis.

Also, like the handle assembly 130, in some example configurations, the handle assembly 310 may include a force gauge 314 configured to measure an amount of pulling force that the handle assembly 310 is exerting on the tubular member 302. In addition or alternatively, one or more sensors 316 may be disposed on the outer surface of the dilation member 308, and configured to sense an amount of elongation of the dilation member 308 in response to the handle assembly 310 proximally pulling the dilation member 308 through the stricture.

Similar to the dilation member 108, the dilation member 308 may include a proximally-tapered portion 318 and a distally-tapered portion 320. Also, similar to the dilation member 108, the proximally-tapered portion 318 may have an associated longitudinal length suitable for dilating a particular bodily structure. In some embodiments, such as those used to dilate esophageal stricture, the proximally-tapered portion 318 may have an associated longitudinal length in a range of about 25 mm to 230 mm, although other lengths may be possible, depending on the bodily structure and/or the type of patient subjected to the dilation procedure. Also, similar to the dilation member 308, the distally-tapered portion 320 may have a longitudinal length that is the same as or different than the longitudinal length of the proximally-tapered portion 318. In some embodiments, as shown in FIG. 3, the distally-tapered portion 320 is substantially shorter than, such as less than one-half, the longitudinal length of the proximally-tapered portion 318, since the distally-tapered portion 320 is not used for dilation.

The dilation member 308 may be different from the dilation member 108 in that the dilation member 308 may include a different longitudinal cross-sectional profile when in its expanded state. In particular, the proximally-tapered portion 318 may include one or more constant-diameter portions longitudinally disposed in between a smallest diameter portion and a largest diameter portion, as opposed to having a continuous proximal taper in between a smallest diameter portion and a largest-diameter portion.

The one or more constant-diameter portions may longitudinally separate the proximally-tapered portion 318 into one or more discrete sections, segments, or stages 322. Each stage 322 may include a proximally-tapered portion 324 and a constant-diameter portion 326. For each stage 322, the associated constant-diameter portion 326 may provide an associated longitudinal length of relatively constant diameter. In addition, for configurations that include a plurality of stages 322, at least two of the stages 322 have different constant diameters over their respective lengths relative to each other. In particular example configurations that include a plurality of stages 322, the more distal a given stage 322, the larger its constant diameter relative to the constant diameters of those stages 322 proximal to the given stage 322, and the more proximal a given stage 322, the smaller its constant diameter relative to the constant diameters of those stages 322 distal to the given stage 322.

The example configuration shown in FIG. 3 includes a plurality of stages, and in particular three stages 322, including a first stage 322(1), a second stage 322(2), and a third stage 322(3). Other example configurations may include more or fewer than three stages. The first stage 322(1) includes a first proximally-tapered portion 324(1) and a first constant-diameter portion 326(1), the second stage 322(2) includes a second proximally-tapered portion 324(2) and a second constant-diameter portion 326(2), and the third stage 322(3) includes a third proximally-tapered portion 324(3) and a third constant-diameter portion 326(3).

Over a longitudinal length of the proximally-tapered portion 318, the third or distal-most constant-diameter portion 326(3) provides the largest or maximum diameter of the proximally-tapered portion 318, and a proximal end 328 provides a smallest diameter of the proximally-tapered portion 318. The first and second constant-diameter portions 326(1), 326(2) are the constant-diameter portions longitudinally disposed in between the smallest diameter and the largest diameter of the proximally-tapered portion 318.

Additionally, among the constant-diameter portions 326, the constant-diameter portions 326 have distally increasing diameters, with the proximal-most constant diameter portion having the smallest diameter among the diameters of the constant-diameter portions 326, and the distal-most constant diameter portion having the largest diameter among the diameters of the constant diameter portions 326. The distal-most constant-diameter portion 326 may be referred to as the maximum diameter portion of the plurality of constant-diameter portions, and the proximal-most constant diameter portion may be referred to as the minimum diameter portion of the plurality of constant-diameter portions. In some embodiments, such as those used to dilate esophageal strictures, the diameter of the maximum (distal-most) constant-diameter portion (which is also the maximum diameter of the proximally-tapered portion 318 and/or the dilation member 308), may be in a range of about 8 mm to 20 mm, although other maximum diameters may be possible, depending on the bodily structure and/or the type of patient subjected to the dilation procedure.

For the three-stage configuration of FIG. 3, the first, proximal-most constant-diameter portion 326(1) has the smallest diameter of the three constant-diameter portions 326, the third, distal-most constant-diameter portion 326(3) has the largest diameter of the three constant diameter portions 326, and the second, intermediate constant-diameter portion 326(2) has a diameter that is larger than the diameter of the first constant-diameter portion 326(1) and smaller than the diameter of the third constant-diameter portion 326(3).

During a dilation procedure, as the dilation member 308 proximally moves through a stricture, each distally next stage may function to increasingly dilate the stricture (or make the passageway more patent or wider) compared to the proximally previous stage. For example, the second stage 322(2) may dilate the stricture more than the first stage 322(1), and the third stage 322(3) may dilate the stricture more than the second stage 322(2). For a given ith stage 322(i) currently biasing the stricture, since the constant-diameter portion 326(i) is distal to the proximally-tapered portion 324(i), then as the dilation member 308 moves through the stricture, the ith proximally-tapered portion 324(i) may engage with the stricture to continuously widen the stricture. Then, when the ith proximally-tapered portion 324(i) moves proximally past the stricture, the ith constant-diameter portion 326(i) may engage with the stricture, during which time the dilation member 308 does not further dilate the stricture. When the ith constant-diameter portion 326(i) moves proximally past the stricture, then a distally-next proximally-tapered portion 324(i+1) may engage with the stricture to further dilate the stricture. The dilation procedure may proceed in this manner until each of the stages 322 (e.g., each of the three stages 322(1), 322(2), 322(3)) has engaged with and/or biased the stricture. However, at a given point in time during the dilation procedure, should the physician or operator determine to stop dilating before a last, distally-most stage has completely engaged with and dilated the stricture, the physician may deflate or contract the dilation member 308 and withdraw it through the stricture back to outside the patient.

By configuring the dilation member 308 with multiple stages or with at least one constant-diameter portion in between the smallest and largest diameter portions, the dilation member 308 may provide breaks or pauses in between discrete periods of dilation as the dilation member 308 proximally moves through the stricture. That is, as the dilation member 308 proximally moves through the stricture, the proximally-tapered portions 324 function to continuously dilate the stricture, and the constant-diameter portions 326 function to provide breaks or pauses in between the discrete periods of time that the proximally-tapered portions 324 continuously dilate the stricture.

As the dilation member 308 proximally moves through the stricture, during a time period that an ith proximally-tapered portion 324(i) increasingly dilates the stricture, the stricture may provide a continuously increasing resistance to the proximal movement (or a continuously increasing force feedback). Then, during a time period that an ith constant-diameter portion 326(i) engages with the stricture, the stricture may provide a relatively constant resistance to the proximal movement (or a relatively constant force feedback). Accordingly, as the dilation member 308 proximally moves through the stricture, the multiple stages 322 may provide alternating time periods of increasing dilation with increasing force feedback and no dilation with relatively constant force feedback. This configuration is in contrast to the continuous proximal taper configuration of FIG. 1, where the continuous proximally-tapered portion 114 continuously dilates the stricture and provides a continuously increasing resistance or force feedback between the smallest diameter portion and the largest diameter portion as the dilation member 108 proximally moves through the stricture.

In at least some example dilation procedures, the breaks in the dilation that the multi-stage dilation member 308 of FIG. 3 provides may be advantageous over the continuous dilation provided by the continuous taper dilation member 108 of FIG. 1, namely that, as the dilation member 308 proximally moves through the stricture, the periods of breaks or pauses in dilation, and in turn the periods of constant force feedback, may make it easier for the physician to determine if the stricture should be further dilated with a larger-diameter stage of the dilation member 308. In contrast, when the continuously tapered dilation member 108 of FIG. 1 is used, the physician is receiving a continuously changing force feedback amount as the dilation member 108 proximally moves through the stricture, which may make it more difficult to determine if or when the stricture should not be further dilated. Accordingly, the periods of constant force feedback provided by the multi-stage dilation member 308 of FIG. 3 may reduce the likelihood that the tissue will perforate, compared to when the dilation member 108 of FIG. 1 to dilate a stricture.

However, both the dilation member 108 of FIG. 1 and the dilation member 308 of FIG. 3 may be equally or at least similarly advantageous when dilating a stricture in that: both can exert multiple forces on the stricture, including a shearing force, a radial force, and/or a rotational/torsional force; both are wire guidable such that they can be navigated through and dilate relative small strictures; and both dilate in response to proximal movement through the stricture due to a proximally pulling action, which may be a more controlled action compared to a pushing action that distally advances a dilation member through the stricture to dilate the stricture.

In addition, for at least some example configurations, over a longitudinal length of the proximally-tapered portion 318, extending from the maximum (distal-most) constant-diameter portion 326(3) to a proximal constant-diameter portion proximal to the maximum constant diameter portion 326 (3)—the proximal constant-diameter portion being either the first constant diameter portion 326(1) or the second constant-diameter portion 326(2) of the three-stage configuration of FIG. 3—the dilation member 308 does not have a diameter that is smaller than the diameter of the proximal constant-diameter portion. In other words, distally over the longitudinal length, the diameter of the dilation member 308 either stays the same or increases.

Such configurations may be in contrast to other expandable dilation member configurations that have a decreasing diameter over a similar longitudinal length. These other configurations may be used to perform dilation procedures that only dilate the stricture through radial expansion, and not through proximal movement (pulling). Such other dilation member configurations may similarly have a plurality of stages of different diameters. The different stages may be sequentially used in an order of increasing diameter. After dilating the stricture with a smaller-diameter stage, the dilation member may be deflated, and then, in its deflated form, longitudinally moved (positioned) so that a larger-diameter stage is aligned with the stricture. The dilation member may then be inflated so that the larger-diameter stage engages with the stricture and radially biases it to further dilate it. The dilation member is then again deflated and longitudinally moved so that a next larger-diameter stage can further dilate the stricture upon inflation. Expandable dilation members used with such dilation procedures may have distally decreasing diameter segments over the longitudinal length to form an outer surface having a relatively constant diameter portion disposed between increasing and decreasing diameter portions that can securely hold the stricture in a longitudinal position—so as to withstand any biasing that causes the stricture to want to longitudinally move—as the dilation member radially expands to dilate the stricture.

In contrast, the expandable dilation member 308 of the present description dilates when proximally moving through the stricture, not just by radially expanding while longitudinally stationary, and so may not need distally decreasing diameter portions in the proximally-tapered portion 318 that can longitudinally hold the stricture while the dilation member radially biases it. Accordingly, as shown in FIG. 3, over the longitudinal length of the proximally-tapered portion 318, distally, the diameter of the dilation member 308 is either constant or increases.

Other configurations of a dilation member that includes one or more stages 322 are possible, including a single-stage configuration that includes a single stage 322, or a multi-stage configuration that includes two stages or four or more stages. Other multi-stage configurations may be similarly configured as the three-stage configuration shown in FIG. 3, except that they have more or a fewer number of stages than three. For a single-stage configuration, a single stage 322 may include a first proximally-tapered portion 324 extending from the proximal end 328 of the dilation member 308 to a proximal end of the constant-diameter portion 326 of the single stage 322. The dilation member 308 may further include a second proximally-tapered portion 324 extending from a distal end of the constant-diameter portion 326 to a proximal end of the distally-tapered portion 320. Various configurations of an expandable dilation member having a proximally-tapered portion that includes at least one constant-diameter portion in between a smallest or minimum diameter and a largest or maximum diameter of the proximally-tapered portion may be possible.

FIGS. 4A-4G illustrate various stages of an example dilation process or procedure that may be performed with the example dilator 300 shown in FIG. 3. Like the dilation process described with reference to FIGS. 2A-2G, the following dilation process is performed to dilate a passageway 330 that is being undesirably narrowed by a stricture 332 of a bodily or anatomical structure 334, such as an esophagus or a pyloric sphincter, as examples. Also, as with the previously described dilation process, the distal portion 306 of the elongate member 302 may be delivered to a treatment site within the patient, which generally includes the stricture 332, the passageway 330 narrowed by the stricture 332, and areas near or adjacent to the stricture 332 where the distal portion 306 and the dilation member 308 may be distally moved to perform the dilation process.

As with the previously described dilation process with reference to FIGS. 2A-2G, since the proximally-tapered portion 318 has a plurality of different diameters over a longitudinal length of the proximally-tapered portion 318, the proximally-tapered portion 118 may dilate the stricture 332 over the plurality of different diameters in response to proximally moving through the stricture 332. As described in further detail below, the proximally-tapered portion 318 may bias the stricture 332 over the plurality of different diameters in response to the proximal movement and during a period of time during which the dilation member 308 remains in its expanded (e.g., inflated) state. That is, the proximally-tapered portion 318 dilates the stricture 332 by biasing the stricture 332 over the plurality of different diameters in response to the proximal movement and without being deflated.

Figure 4A:
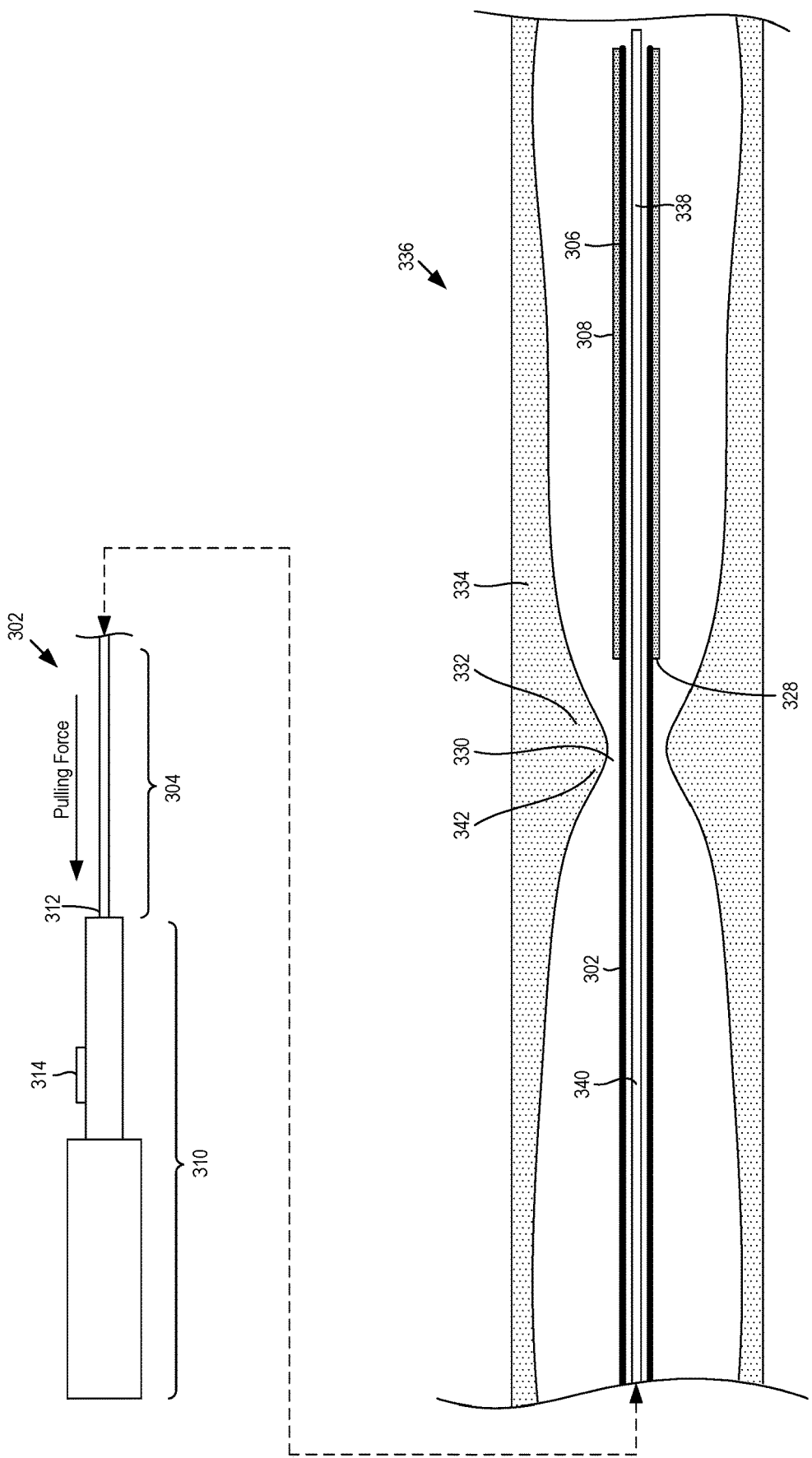
FIG. 4A shows a cross-sectional side view of a distal portion of an elongate member and a dilation member of the dilation device of FIG. 3 positioned distally past a stricture, where the dilation member is configured in an unexpanded state.

Referring to FIG. 4A, as an initial step of the dilation process, a distal portion 338 of a wire guide 340 may be distally advanced from outside of the patient to the treatment site 336. In particular, the distal portion 338 may be distally advanced through the stricture 332 or the passageway 330 so that the distal portion 338 is distally past the stricture 332. As previously mentioned, use of the wire guide 340 may allow the dilation member 308 to move through smaller-sized passageways 330 and/or passageways 330 that are relatively more narrowed or restricted by given strictures.

Figure 4B:
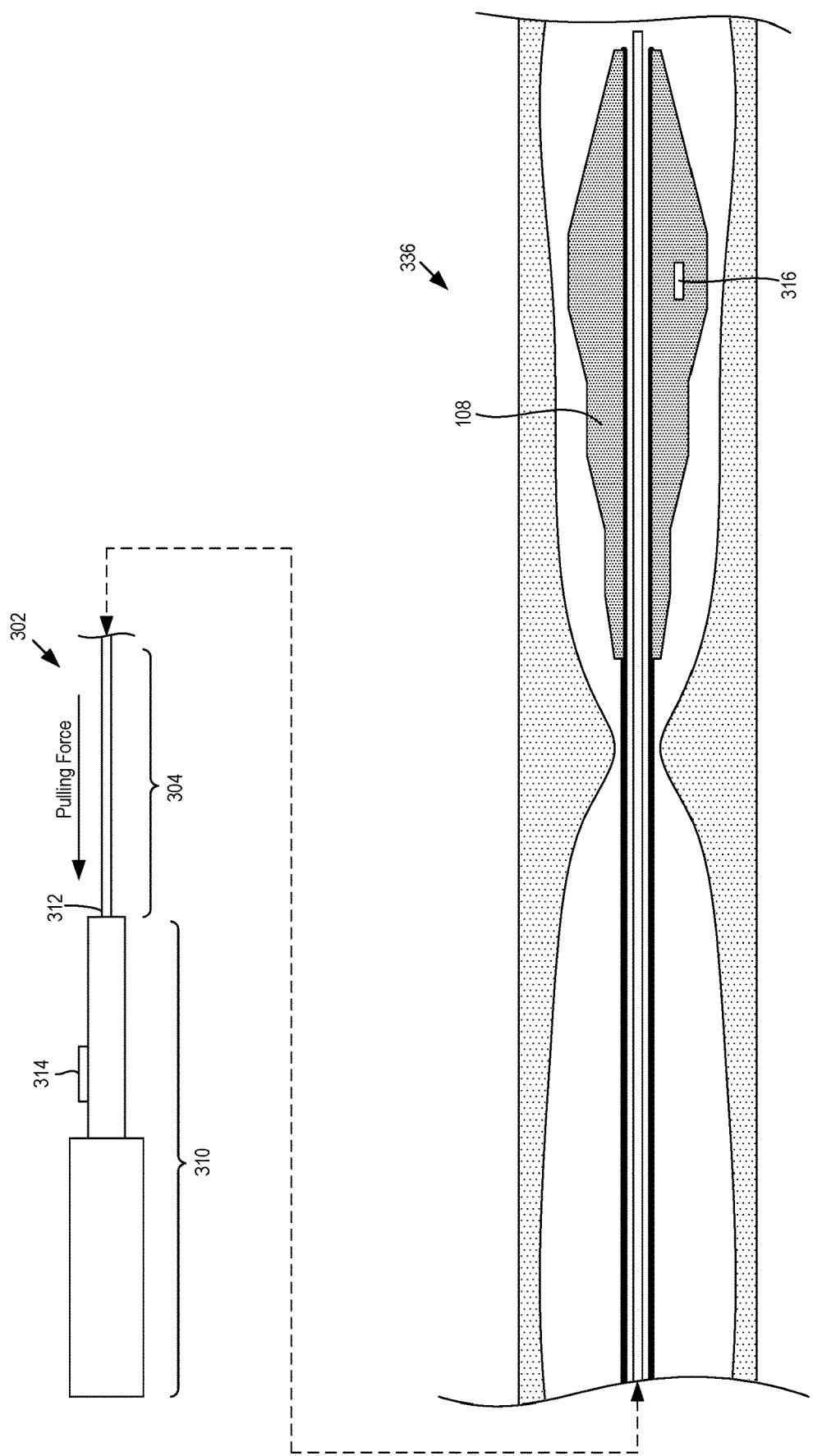
FIG. 4B shows a cross-sectional side view of the distal portion and the dilation member positioned distally past the stricture as in FIG. 42A, but with the dilation member configured in an expanded state.

After the distal portion 338 of the wire guide 340 is at a desired position distally past the stricture 332, the tubular member 302 and the dilation member 308 may be distally advanced over or about the wire guide 340 to the treatment site 336. Like the previously described dilation process, the dilation member 308 may be distally advanced to the treatment site 336 in its unexpanded or contracted state so that the dilation member 308 has a small enough outer diameter over its longitudinal length to distally move through the stricture 332. The distal portion 306 of the tubular member 302 and the dilation member 308 may be distally advanced through the stricture 332 until the proximal end 328 of the dilation member 308 is at a desired location distally past a proximal end 342 of the stricture 332. In some example methods, the desired position may be completely distally past the stricture 332. In other example methods, the desired position may not be completely distally past the stricture 332, but within the passageway 330 defined or circumferentially surrounded by the stricture 332. Referring to FIG. 4B, when the dilation member 308 is in the desired position, the dilation member 308 may be moved or expanded from the unexpanded state to the expanded state, such as by injecting fluid or gas into a cavity of the dilation member 308.

Figure 4C:
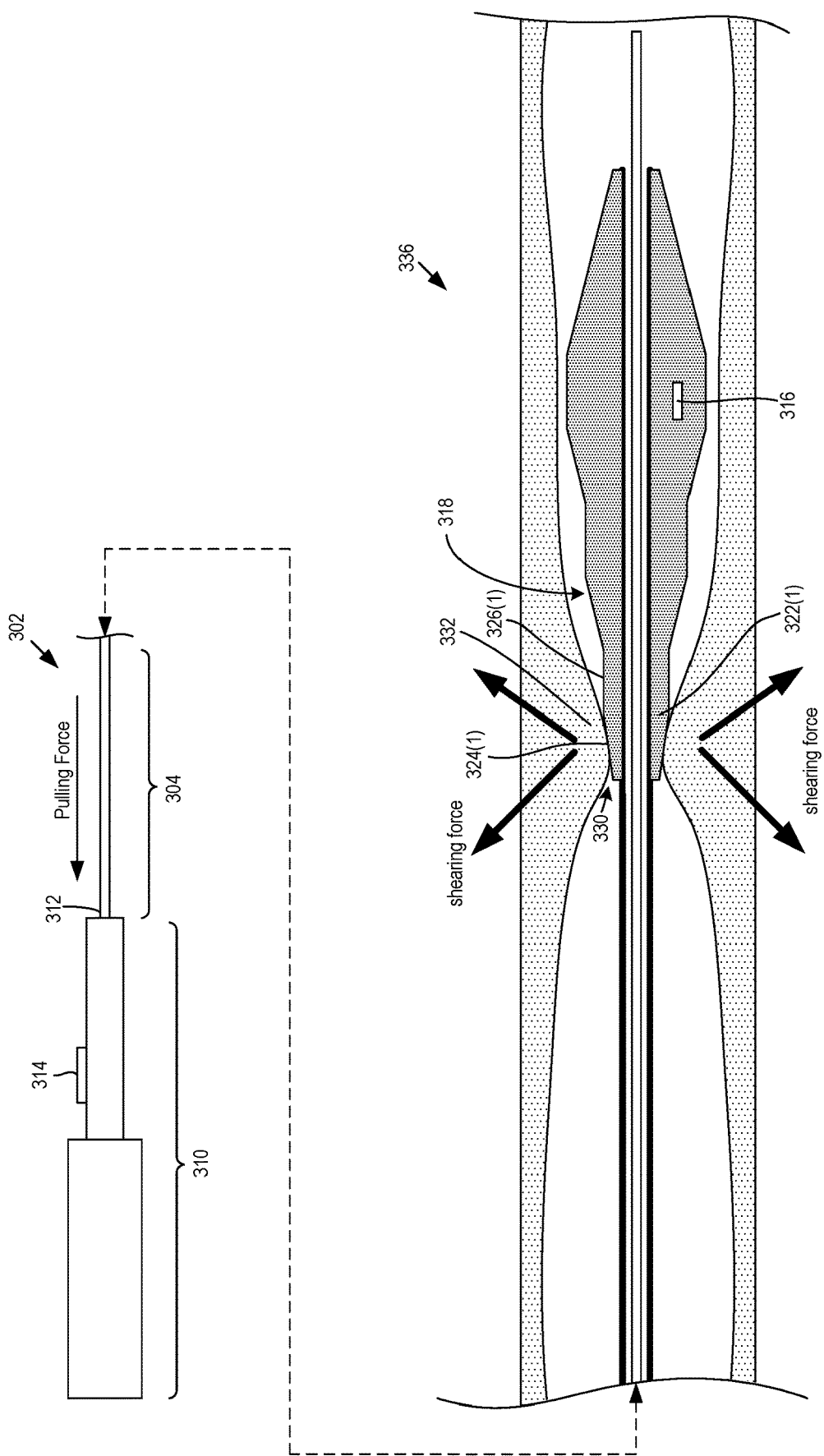
FIG. 4C shows a cross-sectional side view of a proximal-most portion of a proximally-tapered portion of the dilation member in the expanded state engaging with and dilating the stricture by exerting a shearing force on the stricture.

Referring to FIG. 4C, upon being configured in its expanded state, the handle assembly 310 may pull or longitudinally exert a force in a proximal direction on the proximal end 312 of the tubular member 302 to proximally move the proximally-tapered portion 318 of the dilation member 308 through the stricture 332. In response to the proximal movement, the proximally-tapered portion 318 may begin dilating the stricture 332. As with the previously-described dilation process, the proximally-tapered portion 318 may dilate the stricture 332 by biasing the stricture 332 with one or more forces to cause tissue, including muscle fibers, of the stricture 332 to stretch, and in turn widen the passageway 330.

In some example dilation procedures, such as shown in FIG. 3C, the proximal-most proximally-tapered portion of the proximal-most stage—i.e., the first proximally-tapered portion 324(1) of the first stage 322(1)—may be the portion of the proximally-tapered portion 318 that first engages with and begins to dilate the stricture 332. In other example dilation procedures, other portions of the proximally-tapered portion 318 may first contact and/or bias the stricture 332, such as where the size of the passageway 330 is greater than the largest diameter of the first stage 322(1) (i.e., the outer diameter of the first constant-diameter portion 326(1)).

As the handle assembly 310 proximally pulls the dilation member 310 through the stricture 332 such that the proximal-most proximally-tapered portion 324(1) biases the stricture 332, the proximal-most proximally tapered portion 324 may exert a shearing force on the stricture 332, as indicated in FIG. 4C. In addition, the proximal-most proximally-tapered portion 324(1) may exert a radial force on the stricture 332, as was previously described with reference to FIG. 2D. During this time, the stricture 332 may provide an increasing resistance to the proximal movement, or force feedback, as the first proximally-tapered portion 324(1) increasingly dilates the stricture 332. Additionally, for at least some example dilation procedures, the handle assembly 310 may exert an axial rotational force on the tubular member 302, causing the dilation member 308 to axially rotate about its central longitudinal axis as it proximally moves through the stricture, as was previously described with reference to FIG. 2E. The axial rotation may cause the dilation member 308 to exert a rotational or torsional force on the stricture 332 as it proximally moves through the stricture 332.

Figure 4D:
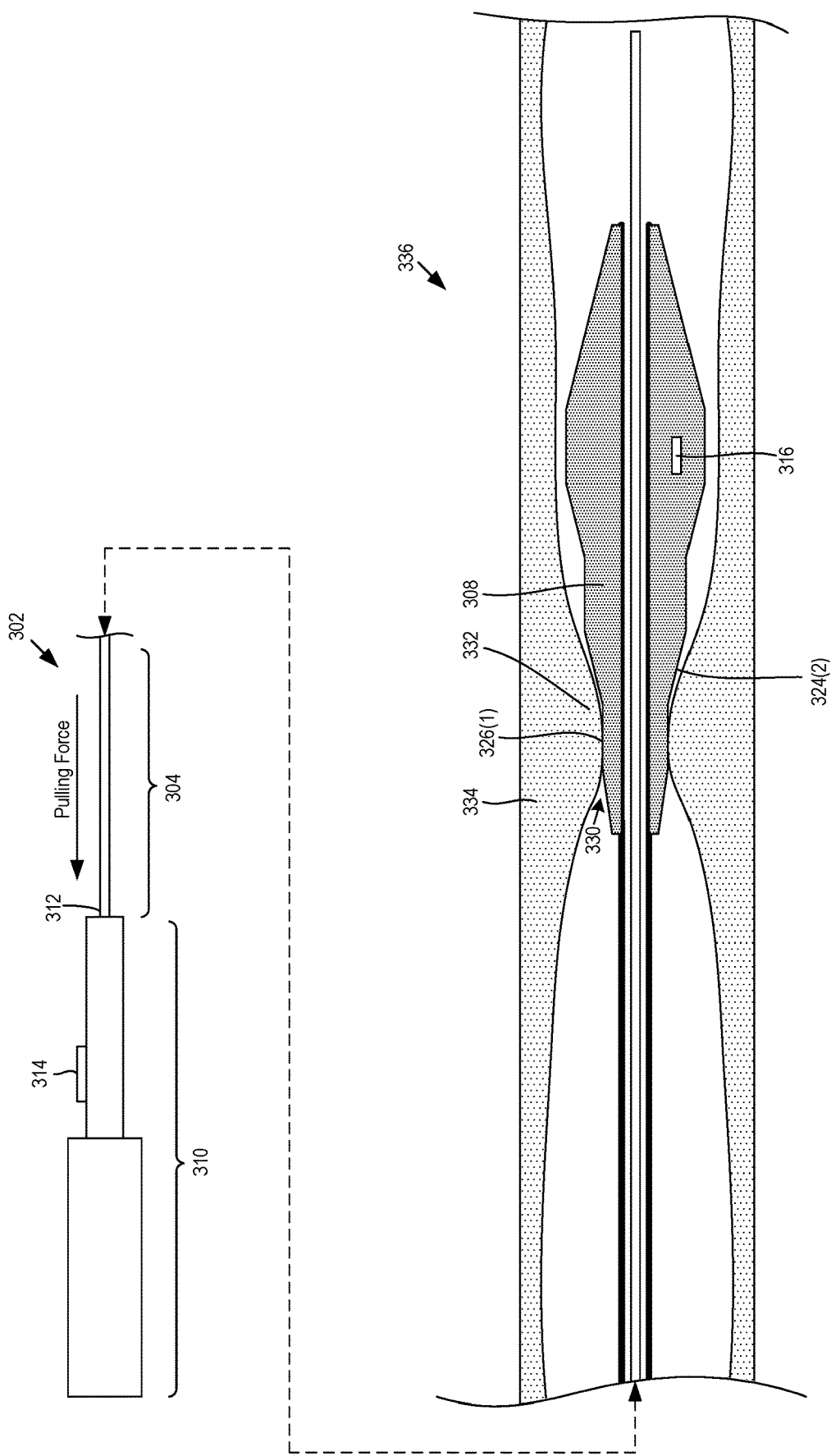
FIG. 4D shows a cross-sectional side view of a proximal-most constant-diameter portion of the proximally-tapered portion of FIG. 4C engaging with the stricture.

Referring to FIG. 4D, the handle assembly 310 may proximally move the dilation member 308 to a position where the first, proximal-most constant-diameter portion 326(1) engages with the stricture 332. During the time that the first constant-diameter portion 326(1) engages with the stricture 332 during proximal movement through the stricture 332, the stricture 332 may provide a relatively constant resistance to the proximal movement, and in turn a relatively constant force feedback to the operator. As the operator operates the handle assembly 310 to move the dilation member 308 while receiving the relatively constant force feedback, the operator may use this break or pause in the constantly-changing (increasing) force feedback to assess whether to continue to dilate the stricture 332. That is, it may be easier for the operator to determine whether to continue to dilate the stricture while sensing a relatively constant force feedback compared to when the force feedback is constantly changing in response to movement through the stricture 332.

Figure 4E:
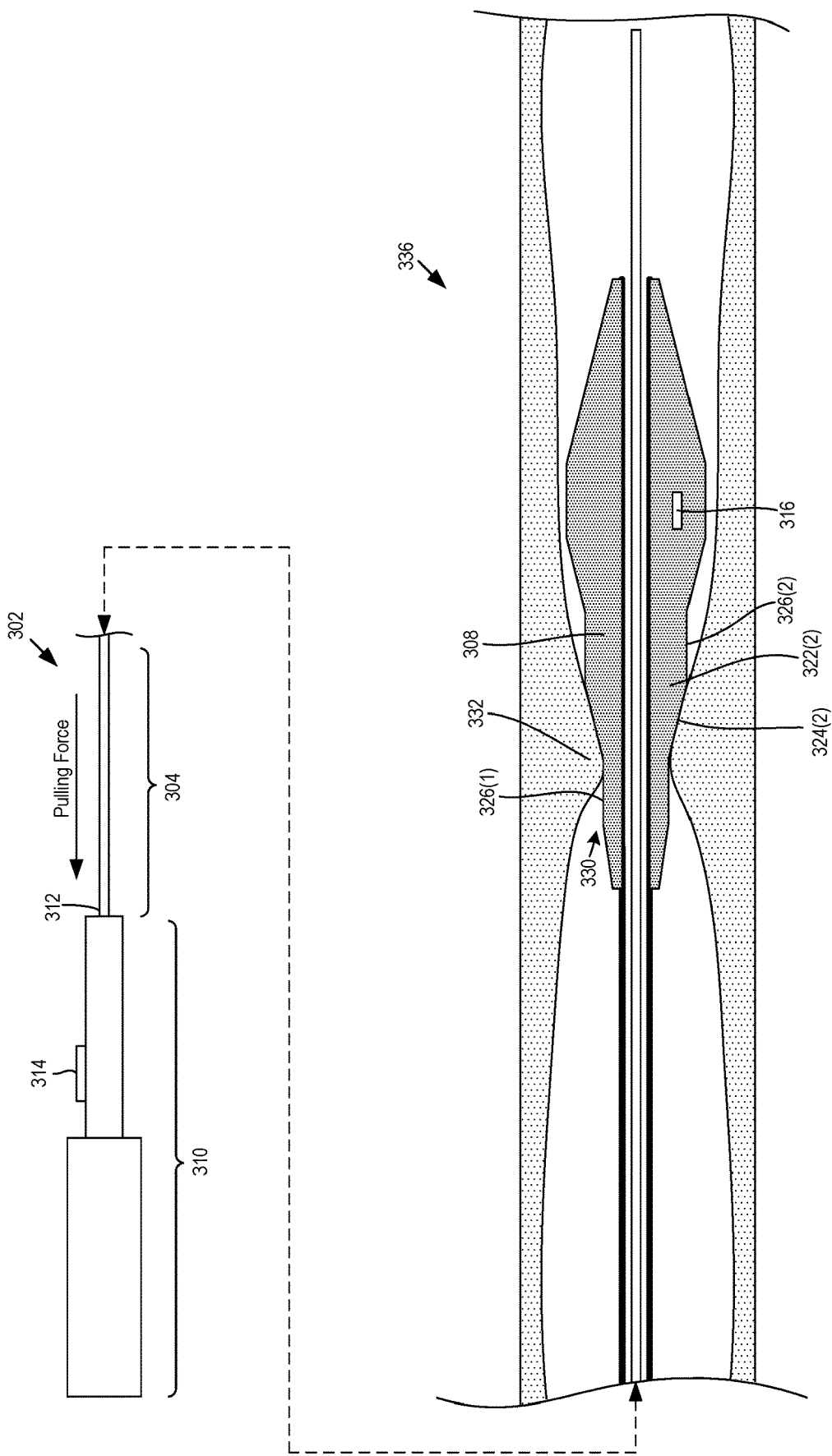
FIG. 4E shows a cross-sectional side view of a distally-next proximally-tapered portion of the dilation member engaging with and dilating the stricture.
Figure 4F:
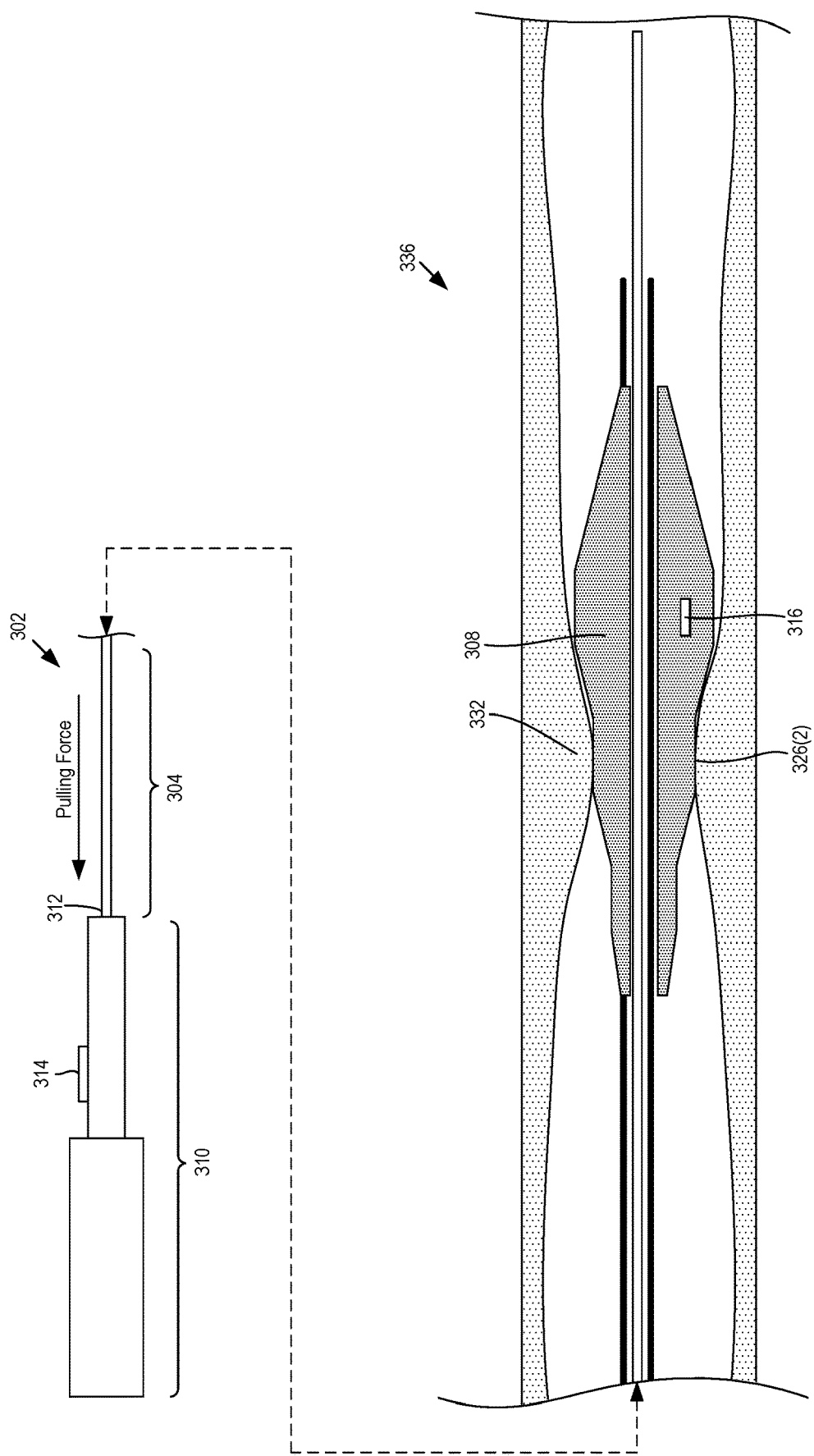
FIG. 4F shows a cross-sectional side view of a distally-next constant-diameter portion of the dilation member engaging with the stricture.

During the period of proximal movement that the first constant-diameter portion 326(1) engages with the stricture 332, if the physician determines that the stricture 332 can be further dilated, the physician may operate the handle assembly 310 to continue to proximally move the dilation member 308 through the stricture 332. In response, a distally next proximally-tapered portion—in this case the second proximally tapered portion 324(2) of the second stage 322(2) may engage with and bias the stricture 332 to further dilate the stricture 332 and widen the passageway 330, as shown in FIG. 4E. Thereafter, provided that the dilation member 308 continues to proximally move through the stricture 332, the second constant-diameter portion 326(2) may engage with the stricture 332, as shown in FIG. 4F.

As previously described, in at least some example configurations, the handle assembly 310 may include a force gauge 314 configured to measure an amount of pulling force that the handle assembly 310 is exerting on the tubular member 302. In addition or alternatively, one or more sensors 316 may be disposed on the outer surface of the dilation member 308, and configured to sense an amount of elongation of the dilation member 308 in response to the handle assembly 310 proximally pulling the dilation member 308 through the stricture 332. In at least some example dilation procedures, in addition or alternatively to the operator using the handle assembly 310 to feel the amount of force feedback, as the dilation member 308 proximally moves through the stricture 332, the force feedback may be constantly or continuously measured by the force gauge 314. An output device coupled to or included with the force gauge 314 may provide an output of or associated with the measured force feedback. For example, the output device may provide a digital read-out of the measured force, which the operator may monitor or observe to determine whether to continue dilating the stricture 332. In addition or alternatively, the force gauge 314 and/or the output device may be configured to continuously compare the force feedback with a force threshold value. The force threshold value may be a predetermined force value associated with a resistive force that has a relatively high degree of causing tissue perforation. In the event that the measured force feedback is within a predetermine range of, reaches, or exceeds the force threshold value, the output device may be configured to output a warning (e.g., audibly, visually, and/or tactile), which may indicate to the operator to stop proximal movement of the dilation member 308 and/or further dilation of the stricture 332.

Referring back to FIG. 4D, if the operator determines not to further dilate the stricture 332, the operator may deflate the dilation member 308 or move the dilation member 308 to its unexpanded state, and proximally remove the distal portion 306 and the dilation member 308 from the patient. Also, in general, at any time during the dilation procedure, the operator may use the force feedback in response to the proximal pulling to determine whether to stop dilation, including during time periods when a proximally-tapered portion of a given stage 322 is dilating the stricture 332. For example, a given ith proximally-tapered portion 324(i) may be biasing the stricture 332, and before the ith constant-diameter portion engages with the stricture 332, the operator may determine that the stricture 332 should not be dilated anymore, in which case the dilation member 308 may stop being proximally moved through the stricture 332 in the expanded state, deflated, and then withdrawn through the stricture from the bodily structure 334 to outside the patient in the unexpanded state.

Figure 4G:
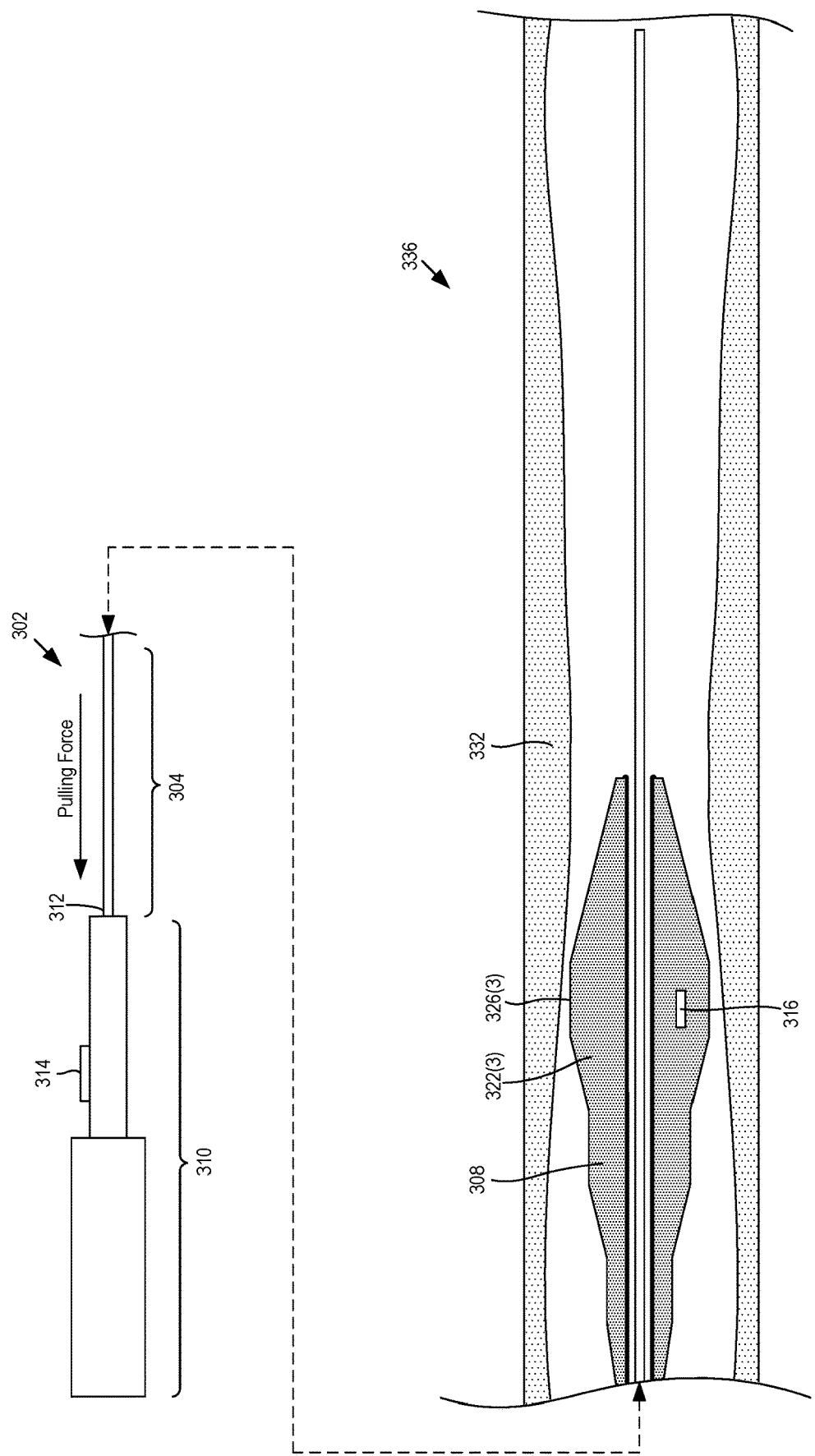
FIG. 4G shows a cross-sectional side view of the dilation member being completely proximally moved through the stricture while in the expanded state.

The dilation procedure may proceed in this manner, where the dilation member 308 dilates the stricture 332 in discrete steps or stages separated by stops or pauses in dilation as the stricture 332 engages with one or more constant-diameter portions 326 disposed in between the smallest diameter portion and the largest diameter portion. FIG. 4G shows the distal-most stage 322(3) having been proximally moved through the stricture 332, with the stricture 332 having been biased and dilated by the largest diameter portion of the dilation member 308, i.e., the constant-diameter portion 326(3) of the last, distal-most stage 322(3).

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method comprising:
   proximally moving a proximally-tapered portion of a dilation member through a stricture of a bodily structure providing a passageway;

dilating the stricture with the proximally-tapered portion in response to proximally moving the proximally-tapered portion through the stricture; and rotating the dilation member while dilating the stricture with the proximally-tapered portion and proximally moving the dilation member through the stricture.

2. The method of claim 1, wherein the proximally-tapered portion comprises a plurality of stages, wherein each of the plurality of stages has an associated length of constant diameter, and wherein the stages have different constant diameters from each other over their respective lengths.

3. The method of claim 2, further comprising:

engaging the stricture with a stage of the plurality of stages over a length of constant diameter associated with the stage in response to proximally moving the proximally-tapered portion through the stricture.

4. The method of claim 3, wherein the stage comprises a first stage and the length of constant diameter comprises a first length of constant diameter, the method further comprising:

engaging the stricture with a second stage of the plurality of stages over a second length of constant diameter associated with the second stage in response to proximally moving the proximally-tapered portion through the stricture, wherein the constant diameter over the second length is greater than the constant diameter over the first length.

5. The method of claim 3, wherein the stage comprises a first stage and the length of constant diameter comprises a first length of constant diameter, the method further comprising:

engaging the stricture with a proximal taper of a second stage of the plurality of stages in response to proximally moving the proximally-tapered region through the stricture; and in response to engaging the stricture with the proximal taper, deflating the dilation member before engaging the stricture with the second stage over a second length of constant diameter associated with the second stage; and proximally withdrawing the dilation member from the bodily structure in response to deflating the dilation member.

6. The method of claim 1, wherein the proximally-tapered portion comprises a continuously decreasing diameter of a length of the proximal portion in a proximal direction.

7. The method of claim 6, wherein the proximally-tapered portion comprises an angle relative to a central axis of the dilation member in a range of 2 to 6.5 degrees.

8. The method of claim 1, further comprising:

positioning a proximal end of the dilation member distally past a proximal end of the stricture by distally advancing the dilation member in an unexpanded state through the stricture until the proximal end of the dilation member is at a position distally past the proximal end of the stricture;

in response to positioning the proximal end of the dilation member, changing the dilation member from the unexpanded state to the expanded state.

9. The method of claim 1, measuring a resistance to the proximally moving of the dilation member provided by the stricture by measuring, with a force gauge, an amount of longitudinal force proximally moving the elongate member.

10. The method of claim 1, sensing, with at least one sensor attached to the dilation member, an amount of elongation of the dilation member in response to proximally moving the dilation member.

11. The method of claim 1, wherein the dilation member comprises a dilation balloon.

12. The method of claim 1, wherein the bodily structure comprises an esophagus of the patient.

13. The method of claim 1, wherein the bodily structure comprises a pyloric sphincter.

* * * * *